(12) United States Patent
Smith et al.

(10) Patent No.: US 12,263,019 B2
(45) Date of Patent: Apr. 1, 2025

(54) APPARATUS AND A METHOD FOR THE GENERATION OF A PLURALITY OF PERSONAL TARGETS

(71) Applicant: Strategic Coach, Toronto (CA)

(72) Inventors: Barbara Sue Smith, Toronto (CA); Daniel J. Sullivan, Toronto (CA)

(73) Assignee: The Strategic Coach Inc., Toronto (CA)

( * ) Notice: Subject to any disclaimer, the term of this patent is extended or adjusted under 35 U.S.C. 154(b) by 0 days.

(21) Appl. No.: 18/142,508

(22) Filed: May 2, 2023

(65) Prior Publication Data

US 2024/0366158 A1 Nov. 7, 2024

(51) Int. Cl.
*A61B 5/00* (2006.01)
*H04L 51/02* (2022.01)
*H04L 67/306* (2022.01)

(52) U.S. Cl.
CPC ............ *A61B 5/7275* (2013.01); *H04L 51/02* (2013.01); *H04L 67/306* (2013.01)

(58) Field of Classification Search
CPC ...... A61B 5/7275; H04L 51/02; H04L 67/306
See application file for complete search history.

(56) References Cited

U.S. PATENT DOCUMENTS

| | | | |
|---|---|---|---|
| 9,672,482 B2 | 6/2017 | Rubin | |
| 10,997,660 B1 | 5/2021 | Webster | |
| 2008/0201269 A1* | 8/2008 | Hollins | G06Q 40/04 705/36 R |
| 2009/0106136 A1* | 4/2009 | Wright | G06Q 40/06 705/35 |
| 2016/0275614 A1* | 9/2016 | Dintenfass | G16Z 99/00 |
| 2016/0321935 A1 | 11/2016 | Mohler | |
| 2017/0103180 A1* | 4/2017 | Jiao | G16H 50/30 |
| 2017/0277853 A1* | 9/2017 | Carlson | G16H 50/30 |
| 2019/0147529 A1* | 5/2019 | Wright | G06Q 40/06 705/36 R |
| 2019/0259499 A1* | 8/2019 | Hong | G16H 50/20 |
| 2019/0378207 A1* | 12/2019 | Dibner-Dunlap | H04L 67/535 |
| 2020/0005928 A1* | 1/2020 | Daniel | G16H 15/00 |

(Continued)

FOREIGN PATENT DOCUMENTS

AU 2016210760 A1 8/2016

*Primary Examiner* — Lena Najarian
*Assistant Examiner* — Pierre L Maccagno
(74) *Attorney, Agent, or Firm* — Caldwell Intellectual Property Law

(57) ABSTRACT

An apparatus for the generation of a plurality of personal targets is disclosed. The apparatus comprises at least a processor and a memory communicatively connected to the at least a processor. The memory instructs the processor to extract a user profile from a user, wherein a user profile comprises a plurality of user data. The memory then instructs the processor to extract a user profile from a user, wherein a user profile comprises a plurality of user data. The memory instructs the processor to determine tenure data as a function of the user data. The memory instructs the processor to predict forecast data as a function of the tenure data and the user data. The memory instructs the processor to generate a plurality of personal targets as a function of the forecast data. The memory then instructs the processor to display the data using a display device.

14 Claims, 10 Drawing Sheets

(56) References Cited

U.S. PATENT DOCUMENTS

| | | | |
|---|---|---|---|
| 2021/0065907 A1* | 3/2021 | Neumann | G16H 20/00 |
| 2021/0098099 A1* | 4/2021 | Neumann | G06F 18/24147 |
| 2021/0319887 A1* | 10/2021 | Derrick, Jr. | A61B 5/7275 |
| 2021/0343406 A1* | 11/2021 | McMillan | G06F 16/244 |
| 2022/0115114 A1* | 4/2022 | Johnston | G16H 20/60 |
| 2022/0129988 A1* | 4/2022 | Faucher-Courchesne | G06N 20/00 |
| 2022/0208347 A1* | 6/2022 | Neumann | G06N 20/00 |
| 2023/0099519 A1* | 3/2023 | Beltran | G16H 50/20 600/300 |

* cited by examiner

APPARATUS AND A METHOD FOR THE GENERATION OF A PLURALITY OF PERSONAL TARGETS

FIELD OF THE INVENTION

The present invention generally relates to the field of artificial intelligence. In particular, the present invention is directed to an apparatus and a method for the generation of a plurality of personal targets.

BACKGROUND

Computing devices have struggled to associate predictions with user data. Inaccurate harvesting of information from a user has led to an inaccurate prediction of details associated with a user. Accurate predictions of monetary resources and lifespan have long been an inexact science that has led to an inefficient management of resources.

SUMMARY OF THE DISCLOSURE

In an aspect, an apparatus for the generation of a plurality of personal targets. The apparatus comprises at least a processor and a memory communicatively connected to the at least a processor. The memory instructs the processor to extract a user profile from a user, wherein a user profile comprises a plurality of user data. The memory then instructs the processor to extract a user profile from a user, wherein a user profile comprises a plurality of user data. The memory instructs the processor to determine tenure data as a function of the user data. The memory instructs the processor to predict forecast data as a function of the tenure data and the user data. The memory instructs the processor to generate a plurality of personal targets as a function of the forecast data. The memory then instructs the processor to display the plurality of personal targets and the forecast data using a display device.

In another aspect, a method for the generation of a plurality of personal targets is disclosed. The method comprises extracting, using at least a processor, a user profile from a user, wherein a user profile comprises a plurality of user data. The method comprises determining, using the at least a processor, tenure data as a function of the user data. The method comprises predicting, using the at least a processor, forecast data as a function of the tenure data. The method comprises generating, using the at least a processor, a plurality of personal targets as a function of the forecast data, wherein each personal target of the plurality of personal targets are associated with a timeline. The method comprises displaying, using a display device, the plurality of personal targets and the forecast data.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

The drawings are not necessarily to scale and may be illustrated by phantom lines, diagrammatic representations and fragmentary views. In certain instances, details that are not necessary for an understanding of the embodiments or that render other details difficult to perceive may have been omitted.

DETAILED DESCRIPTION

At a high level, aspects of the present disclosure are directed to an apparatus for the generation of a plurality of personal targets is disclosed. The apparatus comprises at least a processor and a memory communicatively connected to the at least a processor. The memory instructs the processor to extract a user profile from a user, wherein a user profile comprises a plurality of user data. The memory then instructs the processor to extract a user profile from a user, wherein a user profile comprises a plurality of user data. The memory instructs the processor to determine tenure data as a function of the user data. The memory instructs the processor to predict forecast data as a function of the tenure data and the user data. The memory instructs the processor to generate a plurality of personal targets as a function of the forecast data. The memory then instructs the processor to display the plurality of personal targets and the forecast data using a display device. Exemplary embodiments illustrating aspects of the present disclosure are described below in the context of several specific examples.

Figure 1:
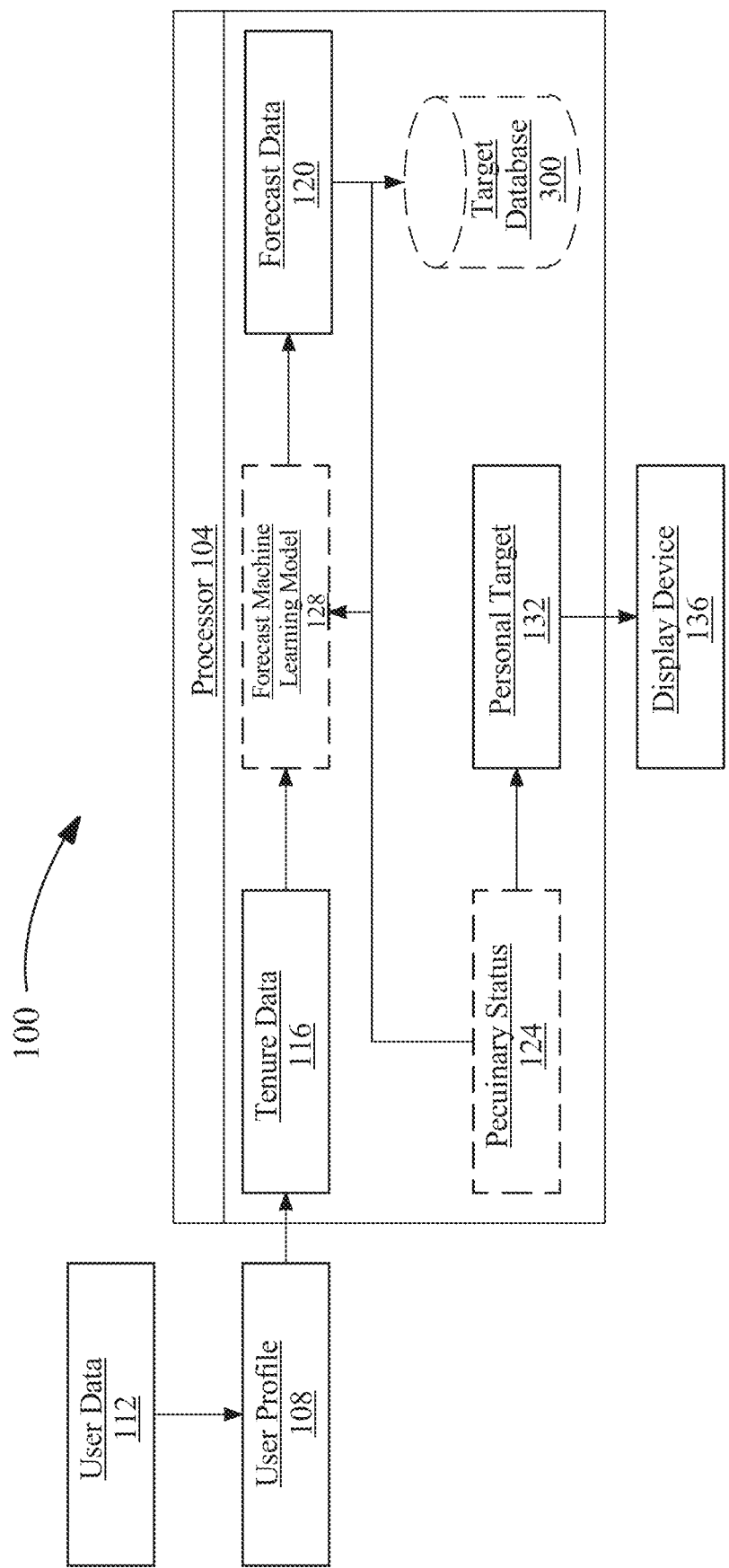
FIG. 1 is a block diagram of an exemplary embodiment of an apparatus for the generation of a plurality of personal targets.

Referring now to FIG. 1, an exemplary embodiment of an apparatus 100 for the generation of a plurality of personal targets is illustrated. Apparatus 100 includes a processor 104. Processor 104 may include any computing device as described in this disclosure, including without limitation a microcontroller, microprocessor, digital signal processor (DSP) and/or system on a chip (SoC) as described in this disclosure. Computing device may include, be included in, and/or communicate with a mobile device such as a mobile telephone or smartphone. Processor 104 may include a single computing device operating independently, or may include two or more computing device operating in concert, in parallel, sequentially or the like; two or more computing devices may be included together in a single computing device or in two or more computing devices. Processor 104 may interface or communicate with one or more additional devices as described below in further detail via a network interface device. Network interface device may be utilized for connecting processor 104 to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network may employ a wired and/or a wireless mode of communication. In general, any network topology may be used. Information (e.g., data, software etc.) may be communicated to and/or from a computer and/or a computing device. Processor 104 may include but is not limited to, for example, a computing device or cluster of computing devices in a first location and a second computing device or cluster of computing devices in a second location. Processor 104 may include one or more computing devices dedicated to data storage, security, distribution of traffic for load balancing, and the like. Processor 104 may distribute one or more computing tasks as described below across a plurality of computing devices of computing device, which may operate in parallel, in series, redundantly, or in any other manner used for distribution of tasks or memory between computing devices. Processor 104 may be implemented using a "shared nothing" architecture in which data is cached at the worker, in an embodiment, this may enable scalability of apparatus 100 and/or computing device.

With continued reference to FIG. 1, processor 104 may be designed and/or configured to perform any method, method step, or sequence of method steps in any embodiment described in this disclosure, in any order and with any degree of repetition. For instance, processor 104 may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. Processor 104 may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

With continued reference to FIG. 1, as used in this disclosure, "communicatively connected" means connected by way of a connection, attachment, or linkage between two or more relata which allows for reception and/or transmittance of information therebetween. For example, and without limitation, this connection may be wired or wireless, direct, or indirect, and between two or more components, circuits, devices, systems, apparatus, and the like, which allows for reception and/or transmittance of data and/or signal(s) therebetween. Data and/or signals therebetween may include, without limitation, electrical, electromagnetic, magnetic, video, audio, radio, and microwave data and/or signals, combinations thereof, and the like, among others. A communicative connection may be achieved, for example, and without limitation, through wired or wireless electronic, digital, or analog, communication, either directly or by way of one or more intervening devices or components. Further, communicative connection may include electrically coupling or connecting at least an output of one device, component, or circuit to at least an input of another device, component, or circuit. For example, without limitation, via a bus or other facility for intercommunication between elements of a computing device. Communicative connecting may also include indirect connections via, for example, and without limitation, wireless connection, radio communication, low power wide area network, optical communication, magnetic, capacitive, or optical coupling, and the like. In some instances, the terminology "communicatively coupled" may be used in place of communicatively connected in this disclosure.

With continued reference to FIG. 1, processor 104 may be configured to extract a user profile 108 from a user. For the purposes of this disclosure, a "user profile" is a representation of information and/or data describing information associated with a user. A user profile 108 may be made up of a plurality of user data 112. As used in the current disclosure, "user data" is information associated with the user. User profile 108 may be associated with an individual user or the user's business. A user profile 108 may be created by a processor 104, a user, or a third party. The user profile 108 may include at least any of the following personal information: age, height, gender, credit, geographical location, financial information, criminal history, medical history, and the like. A user profile 108 may additionally include information regarding the user's business. This may include revenue, gross income, net income, business debts, a list of business expenses, current inventory, inventory history, sales information, human resource information, employee information, employee salaries, time cards, a list of company assets, a list of capital projects, accounting information, and the like. User data 112 may include pecuniary data and health data. As used in the current disclosure, "pecuniary data" is an element of data that is related to a user's assets, income, and debts. Pecuniary data may include any financial record associated with the user, this may include bank statements, credit card statements, investment portfolios, all assets, debts, liabilities, and the like. As used in the current disclosure, "health data" is an element of data that is related to a user's current health. Health data may include test results, medical records, family medical history, list of medical conditions, physician notes, medical facility records, and the like. In a non-limiting example, the user profile may be the same or substantially the same as the entity profile described in U.S. patent application Ser. No. 18/141,320, filed on Apr. 28, 2023, titled "METHOD AND AN APPARATUS FOR ROUTINE IMPROVEMENT FOR AN ENTITY," which is incorporated by reference herein in its entirety.

With continued reference to FIG. 1, a user profile 108 may be received by process 104 via user input. For example, and without limitation, the user or a third party may manually input user profile 108 using a graphical user interface of processor 104 or a remote device, such as for example, a smartphone or laptop. The user profile 108 may additionally be generated via the answer to a series of questions. The series of questions may be implemented using a chatbot, as described herein below. A chatbot may be configured to generate questions regarding any element of the user profile 108. In a non-limiting embodiment, a user may be prompted to input specific information or may fill out a questionnaire. In an embodiment, a graphical user interface may display a series of questions to prompt a user for information pertaining to the user profile 108. The user profile 108 may be transmitted to processor 104, such as via a wired or wireless communication, as previously discussed in this disclosure. The user profile 108 can be retrieved from multiple sources third-party sources including the user's inventory records, financial records, human resource records, past user profiles 108, sales records, user notes and observations, and the like. A user profile may be placed through an encryption process for security purposes.

With continued reference to FIG. 1, a user profile 108 may include user records. As used in the current disclosure, a "user record" is a document that contains information regarding the user. User records may include user credentials, reports, financial records, medical records, business records, Asset inventory, and government records (i.e. birth certificates, social security cards, and the like). A user record may additionally include an employee record. An employee record may include things like employee evaluations, human resource records, client files, invoices, time cards, driver's license databases, news articles, social media profiles and/or posts, and the like. User records may be identified using a web crawler. User records may include a variety of types of "notes" entered over time by the user, employees of the user, support staff, advisors, and the like. User records may be converted into machine-encoded text using an optical character reader (OCR).

Still referring to FIG. 1, in some embodiments, optical character recognition or optical character reader (OCR) includes automatic conversion of images of written (e.g., typed, handwritten, or printed text) into machine-encoded text. In some cases, recognition of at least a keyword from an image component may include one or more processes, including without limitation optical character recognition (OCR), optical word recognition, intelligent character recognition, intelligent word recognition, and the like. In some cases, OCR may recognize written text, one glyph or character at a time. In some cases, optical word recognition may recognize written text, one word at a time, for example, for languages that use a space as a word divider. In some cases, intelligent character recognition (ICR) may recognize written text one glyph or character at a time, for instance by employing machine learning processes. In some cases, intelligent word recognition (IWR) may recognize written text, one word at a time, for instance by employing machine learning processes.

Still referring to FIG. 1, in some cases, OCR may be an "offline" process, which analyses a static document or image frame. In some cases, handwriting movement analysis can be used as input for handwriting recognition. For example, instead of merely using shapes of glyphs and words, this technique may capture motions, such as the order in which segments are drawn, the direction, and the pattern of putting the pen down and lifting it. This additional information can make handwriting recognition more accurate. In some cases, this technology may be referred to as "online" character recognition, dynamic character recognition, real-time character recognition, and intelligent character recognition.

Still referring to FIG. 1, in some cases, OCR processes may employ pre-processing of image components. Pre-processing process may include without limitation de-skew, de-speckle, binarization, line removal, layout analysis or "zoning," line and word detection, script recognition, character isolation or "segmentation," and normalization. In some cases, a de-skew process may include applying a transform (e.g., homography or affine transform) to the image component to align text. In some cases, a de-speckle process may include removing positive and negative spots and/or smoothing edges. In some cases, a binarization process may include converting an image from color or greyscale to black-and-white (i.e., a binary image). Binarization may be performed as a simple way of separating text (or any other desired image component) from the background of the image component. In some cases, binarization may be required for example if an employed OCR algorithm only works on binary images. In some cases, a line removal process may include the removal of non-glyph or non-character imagery (e.g., boxes and lines). In some cases, a layout analysis or "zoning" process may identify columns, paragraphs, captions, and the like as distinct blocks. In some cases, a line and word detection process may establish a baseline for word and character shapes and separate words, if necessary. In some cases, a script recognition process may, for example in multilingual documents, identify a script allowing an appropriate OCR algorithm to be selected. In some cases, a character isolation or "segmentation" process may separate signal characters, for example, character-based OCR algorithms. In some cases, a normalization process may normalize the aspect ratio and/or scale of the image component.

Still referring to FIG. 1, in some embodiments, an OCR process will include an OCR algorithm. Exemplary OCR algorithms include matrix-matching process and/or feature extraction processes. Matrix matching may involve comparing an image to a stored glyph on a pixel-by-pixel basis. In some cases, matrix matching may also be known as "pattern matching," "pattern recognition," and/or "image correlation." Matrix matching may rely on an input glyph being correctly isolated from the rest of the image component. Matrix matching may also rely on a stored glyph being in a similar font and at the same scale as input glyph. Matrix matching may work best with typewritten text.

Still referring to FIG. 1, in some embodiments, an OCR process may include a feature extraction process. In some cases, feature extraction may decompose a glyph into features. Exemplary non-limiting features may include corners, edges, lines, closed loops, line direction, line intersections, and the like. In some cases, feature extraction may reduce dimensionality of representation and may make the recognition process computationally more efficient. In some cases, extracted feature can be compared with an abstract vector-like representation of a character, which might reduce to one or more glyph prototypes. General techniques of feature detection in computer vision are applicable to this type of OCR. In some embodiments, machine-learning process like nearest neighbor classifiers (e.g., k-nearest neighbors algorithm) can be used to compare image features with stored glyph features and choose a nearest match. OCR may employ any machine-learning process described in this disclosure, for example machine-learning processes described with reference to FIGS. 5-7. Exemplary non-limiting OCR software includes Cuneiform and Tesseract. Cuneiform is a multi-language, open-source optical character recognition system originally developed by Cognitive Technologies of Moscow, Russia. Tesseract is free OCR software originally developed by Hewlett-Packard of Palo Alto, California, United States.

Still referring to FIG. 1, in some cases, OCR may employ a two-pass approach to character recognition. The second pass may include adaptive recognition and use letter shapes recognized with high confidence on a first pass to recognize better remaining letters on the second pass. In some cases, two-pass approach may be advantageous for unusual fonts or low-quality image components where visual verbal content may be distorted. Another exemplary OCR software tool include OCRopus. OCRopus development is led by German Research Centre for Artificial Intelligence in Kaiserslautern, Germany. In some cases, OCR software may employ neural networks, for example neural networks as taught in reference to FIGS. 2, 4, and 5.

Still referring to FIG. 1, in some cases, OCR may include post-processing. For example, OCR accuracy can be increased, in some cases, if output is constrained by a lexicon. A lexicon may include a list or set of words that are allowed to occur in a document. In some cases, a lexicon may include, for instance, all the words in the English language, or a more technical lexicon for a specific field. In some cases, an output stream may be a plain text stream or file of characters. In some cases, an OCR process may preserve an original layout of visual verbal content. In some cases, near-neighbor analysis can make use of co-occurrence frequencies to correct errors, by noting that certain words are often seen together. For example, "Washington, D.C." is generally far more common in English than "Washington DOC." In some cases, an OCR process may make use of a priori knowledge of grammar for a language being recognized. For example, grammar rules may be used to help determine if a word is likely to be a verb or a noun. Distance conceptualization may be employed for recognition and classification. For example, a Levenshtein distance algorithm may be used in OCR post-processing to further optimize results.

With continued reference to FIG. 1, user profile 108 may be generated using a web crawler. A "web crawler," as used herein, is a program that systematically browses the internet for the purpose of Web indexing. The web crawler may be seeded with platform URLs, wherein the crawler may then visit the next related URL, retrieve the content, index the content, and/or measures the relevance of the content to the topic of interest. In some embodiments, processor 104 may generate a web crawler to compile the user profile 108 and user data 112. The web crawler may be seeded and/or trained with a reputable website, such as the user's business website, to begin the search. A web crawler may be generated by a processor 104. In some embodiments, the web crawler may be trained with information received from a user through a user interface. In some embodiments, the web crawler may be configured to generate a web query. A web query may include search criteria received from a user. For example, a user may submit a plurality of websites for the web crawler to search to extract user records, inventory records, financial records, human resource records, past user profiles 108, sales records, user notes, and observations, based on criteria such as a time, location, and the like.

With continued reference to FIG. 1, a user profile 108 may include biological information associated with the users. As used in the current disclosure, "biological data" is any information related to the user's health or well-being. Biological data may include chemical, biological, physical, and behavioral data relating to a user. Biological data may include information regarding a user's health including medical history, user diet, exercise, sleep, family medical history, and the like. In other embodiments, biological data may include information collected from a standard health screening such as X-rays, MRI, blood test, lab tests, examinations, and the like. In some embodiments, biological data may be extracted from a user using at least a sensor. As used in this disclosure, a "sensor" is a sensor device that produces an electrical output signal for purpose of sensing and monitoring biological events or changes in its environment. In some cases, In some embodiments, the sensor may include one or more processors that perform one or more processing steps as described in this disclosure. In some cases, the sensor may include, without limitation, a temperature sensor, EMG sensor, ECG sensor, airflow sensor, glucometer sensor, pressure sensor, acoustic sensor, image sensor, magnetic field sensor, and the like thereof. In some embodiments, without limitation, the sensor may include a physical sensor, wherein the physical sensor is a device that measures a physical quantity. In some cases, the sensor may convert physical quantity into an output signal which can be read by processor 104. In some embodiments, without limitation, sensor may include a chemical sensor, wherein the chemical sensor is a device that converts a property of a particular analyte into a measurable signal that is proportional to the analyte concentration. In some cases, a chemical sensor may recognize an analyte molecule in a selective way by transforming it into an analytical electrical signal. In some cases, analyte concentration may include, without limitation, PH value, Ca+ concentration, the glucose concentration of body liquid and the like thereof. In some embodiments, without limitation, sensor may include a biosensor, wherein the biosensor is a device that combine biological material with a suitable platform for a detection of pathogenic organisms, carcinogenic, mutagenic, toxic chemicals or for reporting a biological effect. In some cases, a sensor may include, without limitation, a biosensor, electrochemical biosensor, physical biosensor, optical biosensor, wearable biosensor, and the like thereof.

With continued reference to FIG. 1, a processor 104 may extract user data 112 from a user using a wearable device. As used in the current disclosure, a "wearable device" is a computing device that is designed to be worn on a user's body or clothing. The wearable device may detect biological data, user data 112, or wearable device data. In embodiments, a wearable device may include a smart watch, smart ring, fitness tracking device, and the like. As used in the current disclosure, "wearable device data" is data collected by a wearable device. Wearable device data may include data and associated analysis corresponding to, for instance and without limitation, accelerometer data, pedometer data, gyroscope data, electrocardiogramata, electrooculography (EOG) data, bioimpedance data, blood pressure and heart rate monitoring, oxygenation data, biosensors, fitness trackers, force monitors, motion sensors, video and voice capture data, social media platform data, and the like. User profile 108 may be provided by a user or a second individual on behalf of a user, for instance and without limitation a physician, medical professional, nurse, hospice care worker, mental health professional, and the like. User profile 108 may originate from a user questionnaire, graphical user interface (GUI), or any other suitable forum for gathering information regarding user data 112. Persons skilled in the art, upon review of this disclosure in its entirety, will be aware of the various ways in which user data 112 may be collected and provided to the system described herein.

With continued reference to FIG. 1, processor 104 is configured to determine tenure data 116 as a function of user data 112. "Tenure data," as used in this disclosure, is an element of data relating to the predicted life span of a user. In an embodiment, tenure data 116 may predict how long a user will live based on a plurality of social and biological factors specific to the user profile 108. Tenure data 116 may be reflected as a range of time until a user's predicted death. In a non-limiting example, tenure data 116 may indicate that a user will live an additional 25-30 more years or live to the age of 85-90 years old. Tenure data 116 may be calculated using information from the user profile 108 including presence or absence of exercise, frequency of physical activity, biological data, overall stress level, working conditions, eating habits, BMI, substance abuse, lifestyle choices, medical history, family medical history, and the like. These categories may be weighted, meaning certain data may weigh more in the determination of tenure data 116 than others.

With continued reference to FIG. 1, tenure data 116 may comprise physiological data, As used in the current disclosure, "physiological data" is data regarding the physical health of the user. This may include data regarding past or present health conditions, biological data, the results of medical tests, and the like. A user's physical health may include the health of various user systems including the user's circulatory system, digestive system, nervous system, reproductive system, endocrine system, skeletal system, and/or the like. This may additionally include one or more organs within each system within a user's body. Additionally, physiological data may include various information about the user's cells, tissues, bodily fluids, and the like. A user's physiological data may be gathered by using a plurality of tests. As used in the current disclosures, "tests" refers to any medical test used to extract information about a user's systems. Tests may include various blood, imaging, functionality, lab tests, sleep tests, physical evaluations, blood tests, urine tests, stool samples, evaluations by a medical professional, and the like. Examples of tests may include various blood tests like a complete blood count test, a basic metabolic panel, a blood enzyme test, cholesterol tests, triglyceride tests, blood clotting tests, blood glucose tests, blood oxygen tests, and the like. Additional tests that may be used to generate anatomy data may include various imaging tests such as an MRI, Xray, Mammogram, ultrasound, fluoroscopy, pet scans, and the like. A person who is reasonably skilled in the art, after having reviewed the entirety of this disclosure, would appreciate that various types of tests may be used to determine physiological data. Physiological data may additionally be generated as a function of the current age, gender, height, and weight of the user. For example, a user's liver may be healthy for an elderly adult but unhealthy for a young adult. Physiological data may be expressed as a numerical score or a linguistic value. Physiological data may be represented as a score used to reflect the current health of the user. A non-limiting example, of a numerical scale, may include a scale from 1-10, 1-100, 1-1000, and the like, wherein a rating of 1 may represent a user with critical health conditions, whereas a rating of 10 may represent a user in perfect health. Examples of linguistic values may include, "Critical Health," "Poor Health," "Average Health," "Good health," "Excellent Health," and the like. In some embodiments, a numerical score range may be represented by a linguistic value. As used in the current disclosure, a "numerical score range" is a range of scores that are associated with a linguistic value. For example, this may include a score of 0-2 representing "Critical Health" or a score of 8-10 representing "Excellent Health." A user's physical health may be scored by classifying the current user data 112 to examples of user data from third parties who are similarly situated by age, gender, sex, and overall health.

With continued reference to FIG. 1, a numerical score range representing physiological data may be adjusted using linguistic values. Processor 104 may adjust the numerical score range according to the severity of the disease or condition associated. Alternatively, processor 104 may adjust the numerical score range to indicate the impact the disease or condition will have on the user's lifespan. A numerical score range may be determined by comparing the current diseases or conditions of the user to previous iterations of the numerical score ranges. Previous iterations' numerical score ranges may be taken from users who are similarly situated to the current user by disease condition, height, weight, gender, nationality, lifestyle choices, age, and the like. Previous iterations of a numerical score range may be received from database 300. A numerical score range may be generated using a range machine learning model. As used in the current disclosure, a "range machine-learning model" is a machine-learning model that sorts inputs into categories or bins of data, outputting the categories or bins of data and/or labels associated therewith. The range machine-learning model may be consistent with the classifier described below in FIG. 2. Inputs to the range machine-learning model may include a user profile 108, user data 112, physiological data, lifestyle data, examples of numerical score ranges, and the like. Outputs to the range machine-learning model may include a numerical score range. Range training data is a plurality of data entries containing a plurality of inputs that are correlated to a plurality of outputs for training a processor by a machine-learning process to correlate physiological data to examples of numerical score ranges. Range training data may be received from database 300. Range training data may contain information about user profile 108, user data 112, physiological data, lifestyle data, examples of numerical score ranges, and the like. Range training data may be configured to correlate physiological data to examples of numerical score ranges. Classification may be performed using, without limitation, linear classifiers such as without limitation logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers.

With continued reference to FIG. 1, tenure data 116 may include lifestyle data. As used in the current disclosure, "lifestyle data" is data regarding the user's lifestyle. A user's lifestyle may include a grade or rank of a culmination of the user's lifestyle choices. Lifestyle choices may include the user's profession, substance abuse habits, exercise frequency, stress levels, marital status, diet, age, gender, and the like. Processor 104 may generate lifestyle data as a function of user data 112. A user's lifestyle may be evaluated by whether the user's lifestyle choices will have a positive or negative impact on the user's life span or tenure data 116. Lifestyle data may be generated as a function of lifestyle criteria. Lifestyle criteria may be a set of criteria that are known to improve or impair the user's lifespan. A non-limiting example of a lifestyle criterion may include, users who exercise multiple times a week and may have an increased life expectancy of up to an additional 25%. In another non-limiting example, lifestyle criteria may include if a user drinks more than 3 times a week user's life expectancy may decrease by up to 10%. Lifestyle data may be generated by classifying a plurality of user data 112 to two or more lifestyle criteria. Lifestyle data may be expressed as a numerical score or a linguistic value. Lifestyle data may be represented as a score used to reflect the impact of a user's lifestyle choices on a user's lifespan. A non-limiting example, of a numerical scale, may include a scale from 1-10, 1-100, 1-1000, and the like, wherein a rating of 1 may represent a user whose lifestyle choice negatively impacts their lifespan, whereas a rating of 10 may represent a user whose lifestyle choices have positively impacted their lifespan. Examples of linguistic values may include, "Significant Negative Impact," "Negative Impact," "No Impact," "Positive Impact," "Significant Positive Impact," and the like. In some embodiments, a numerical score range may be represented by a linguistic value. For example, this may include a score of 0-2 representing "Significant Negative Impact" or a score of 8-10 representing "Significant Positive Impact." A user's lifestyle choices may be scored by classifying the current user data 112 to examples of user data from third parties who are similarly situated by age, gender, sex, lifestyle choices, and the like.

Still referring to FIG. 1, at least a processor 104 may be configured to generate a health impact factor as a function of physiological data. A "health impact factor," as used in this disclosure, is a calculation used to predict the impact a user's lifestyle data has on their health and/or actual life expectancy. Health impact factor may be a calculation used to demonstrate the trajectory of a user's health if a certain activity is continued. Health Impact factors may be factored into a user's tenure data 116 to determine the impact the actions have on the user's actual life expectancy. Activities that are positive or negative for a user's health may impact health impact factors. Examples of user activities may include diet considerations, exercise habits, substance abuse habits, tobacco abuse, alcohol abuse, sleep schedule, the overall level of stress, mental health, and the like. Each of these habits may be given a multiplier number based on the user's activity. The multiplier may be determined by the longevity and severity of the activity when compared with the user's current health. In a non-limiting example, the action of working out multiple times a week over the course of 4 years may receive a health impact factor of 1.25. This number may then be multiplied by the user's actual life expectancy to demonstrate a 25% addition in the user's life expectancy as a function of the activity. In other embodiments, a user may use harmful illegal drugs several times a week over many years. This may produce a health impact factor of 0.75. This number may then be multiplied by the user's actual life expectancy to demonstrate a 25% reduction in the user's life expectancy. A user's health impact factor may increase or decrease based on the severity of the actions that are taken by the user. In an embodiment, generating a health impact factor may include identifying the habits of a user. The user habits may be identified by a user entry; for instance, and without limitation, at least a processor 104 may provide a user with a questionnaire in the form of one or more data fields requesting that the user identify activities in which the user engaged. Questions presented to a user may include the number of times that a user engages in physical activity during a given period of time such as a day, a week, or a year. Questions may also be directed to the substance abuse and the severity of the said substance abuse. This may include questions about how much and how often a user drinks alcohol or does illegal substances. A user's responses may be verified by an evaluation by a medical professional to ensure accuracy. A medical professional may look for overt signs of activities that may affect a user's health. For example, a user may indicate that they rarely smoke cigarettes, however, upon physical examination of a user's lungs it is apparent that the user is a heavy smoker.

With continued reference to FIG. 1, processor 104 may determine tenure data 116 using a tenure machine-learning model. As used in the current disclosure, a "Tenure machine-learning model" is a machine-learning model that sorts inputs into categories or bins of data, outputting the categories or bins of data and/or labels associated therewith. The tenure machine-learning model may be consistent with the classifier described below in FIG. 2. Inputs to the tenure machine-learning model may include a user profile 108, user data 112 examples of tenure data 116, examples of physiological data, examples of lifestyle data, and the like. Outputs to the tenure machine-learning model may include tenure data 116, health condition data, and health impact factors. Tenure training data is a plurality of data entries containing a plurality of inputs that are correlated to a plurality of outputs for training a processor by a machine-learning process to correlate user data 112 to examples of tenure data 116. In other embodiments, a machine-learning process may be configured to correlate user data 112 to examples of physiological data or user data 112 to examples of lifestyle data. Tenure training data may be received from database 300. Tenure training data may contain information about user profile 108, user data 112 examples of tenure data 116, examples of physiological data, examples of lifestyle data, and the like. Tenure training data may be configured to correlate user data 112 to examples of tenure data 116. Classification may be performed using, without limitation, linear classifiers such as without limitation logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers.

With continued reference to FIG. 1, processor 104 is configured to predict forecast data 120 as a function of the tenure data 116 and the user data 112. As used in the current disclosure, "forecast data" is a prediction of the user's quality of life near the end of the user's life. A user's quality of life may be reflected as a function of the user's health, wealth, social status, physical health, mental health, business status, and the like. Forecast data 120 may be generated using by identifying the user's current quality of life, as reflected by user data 112. An example of the user's current quality of life may include the user's current net worth along with the user's current physiological data. Forecast data 120 associated with the user may comprise a prediction of the user's pecuniary status 124 along with the user's lifestyle status. This prediction may be generated by comparing the pecuniary data and the health data to forecast criteria. As used in the current disclosure, "forecast criteria" is a set of criteria used to predict the user's future quality of life. Forecast criteria may include financial and health categories such as investments, diversity of investments, business health, debt levels, emergency fund, age, height, weight, gender, medical conditions, substance abuse, physical activity, family medical history, and the like. A processor may be configured to evaluate user data 112 in one or more of these categories to predict a forecast data 120. Forecast data 120 may include tracking or predicting the growth of one or more aspects and/or attributes of an entity or user. In an embodiment, the predicting the forecast data 120 may be done in the same or a substantially similar manner the growth data in U.S. patent application Ser. No. 18/141,725, filed on May 1, 2023, titled "APPARATUS AND A METHOD FOR HIGHER-ORDER GROWTH MODELING," which is incorporated by reference herein in its entirety. This may include using a growth simulation, various machine learning models, fuzzy inference sets, and the like.

With continued reference to FIG. 1, forecast data 120 may include pecuniary status 124. As used in the current disclosure, a "pecuniary status" is a prediction of the user's finances near the end of the user's life span as predicted by tenure data 116. Processor 104 may generate a pecuniary status 124 using user data 112 comprising pecuniary data, personal bank records, business bank records, credit card statements, investment portfolios, management agreements, real estate portfolios, mortgage agreements, debt statements, income statements, payroll records, and the like of a user. Processor 104 may assume that the user finances are reasonably consistent apart from outlier events. This prediction may be done by comparing a user's pecuniary data to examples of other users who were similarly situated by age and financial status while taking into account inflation and market changes over the user's life span. Pecuniary status 124 may be described in terms of monetary resources near the user's predicted death. In a non-limiting example, a user's tenure data 116 reflects that they have an additional 35 years to live. Processor 104 may predict a user's pecuniary status 124 by comparing the user's current pecuniary status 124 of a net worth of $500,000 comprising a diversified investment portfolio. Processor 104 compares the user's current pecuniary status 124 to examples of previous users' average returns on a diversified investment portfolio over 35 years. Processor 104 then determines the user's pecuniary status 124 in 35 years assuming the average returns of investment will be $8,000,00.

With continued reference to FIG. 1, processor 104 may be configured to determine a pecuniary status 124 as a function of a geographic datum. As used in the current disclosure, a "geographic datum" is an element of datum used to identify a pecuniary status 124 based on a pre-determined geographic area. Geographic data may be generated via user input, the use of a GPS tracker, or a sensor. This may be done using a device such as a computer, smartphone, laptop, tablet, and the like. The geographic datum may group other users with similar pecuniary status 124 or forecast data 120 as a function of their geographic proximity. In embodiments, Geographic proximity may include any radius from a given point. Geographic proximity may also include a city, county, state, zip code, area code, and the like.

With continued reference to FIG. 1, forecast data 120 may include lifestyle status. As used in the current disclosure, a "lifestyle status" is a prediction of the user's health near the end of the user's life span as predicted by tenure data 116. A user's health may be measured in the same or substantially the same way that physiological data measures the user's physical health, as mentioned herein above. A lifestyle status may include a prediction of health condition data. As used in the current disclosure, "health condition data" is a prediction of future health conditions that may be experienced by the user. Health condition data may be reflected as the probability that the user will get a medical condition or the severity of that medical condition. Additionally, health condition data may comprise a prediction of the future status of the user's current medical conditions. In a non-limiting example, user data 112 indicates that the user has chronic diabetes. Health condition data may predict that the user's diabetes will significantly improve due to favorable lifestyle data indicating that the user is eating healthily and working out. A health condition data may predict health conditions including but non-limited to diabetes, heart disease, high blood pressure, cancer, digestive issues, neurological issues, stroke, arthritis, kidney disease, and the like. Health condition data may be generated as a function of health condition criteria and user data. Health condition criteria are a set of risk factors for health conditions. Health condition criteria may vary from disease to disease. In a non-limiting example, Health condition criteria for diabetes may include a poor diet and obesity combined with a family history of diabetes. When health condition criteria are met processor 104 may predict that a user may get diabetes in the future. Processor 104 may additionally be configured to adjust the tenure data 116 as a function of the health condition data. In a non-limiting example, if a user has tenure data 116 that reflects a life expectancy of an additional 40+ years. Processor 104 may determine as a function of the user data 112 that the user has an 80% chance of developing breast cancer in their lifetime. Tenure data 116 may be reduced by 15 years due to the possibility of the user getting breast cancer.

With continued reference to FIG. 1, processor 104 may predict forecast data 120 using a forecast machine-learning model 128. As used in the current disclosure, a "forecast machine-learning model" is a machine-learning model that sorts inputs into categories or bins of data, outputting the categories or bins of data and/or labels associated therewith. Forecast machine-learning model 128 may be consistent with the classifier described below in FIG. 2. Inputs to the forecast machine-learning model 128 may include user profile 108, user data 112, tenure data 116, physiological data, lifestyle data, examples of forecast data 120, examples of pecuniary status, examples of lifestyle status, and the like. Outputs to the forecast machine-learning model 128 may include pecuniary status, lifestyle status, and forecast data 120. Forecast training data is a plurality of data entries containing a plurality of inputs that are correlated to a plurality of outputs for training a processor by a machine-learning process to correlate user data 112 and tenure data 116 to examples of forecast data 120. Forecast training data may be received from database 300. Forecast training data may contain information about include user profile 108, user data 112, tenure data 116, physiological data, lifestyle data, examples of forecast data 120, examples of pecuniary status, examples of lifestyle status, and the like. Forecast training data may correlate user data 112 and tenure data 116 to examples of forecast data 120. Classification may be performed using, without limitation, linear classifiers such as without limitation logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers.

With continued reference to FIG. 1, a machine-learning model, such as forecast machine-learning model 128, may be implemented as a fuzzy inferencing system. As used in the current disclosure, a "fuzzy inference" is a method that interprets the values in the input vector (i.e., a plurality of user data 112 and examples of forecast data 120) and, based on a set of rules, assigns values to the output vector. A set of fuzzy rules may include a collection of linguistic variables that describe how the system should make a decision regarding classifying an input or controlling an output. An example of linguistic variables may include variables that represent one or more forecast data 120. Examples of linguistic variables may include terms such as a "Poor Quality of Life," "Moderate Quality of Life," and "Excellent Quality of Life." User data 112 and an example of forecast data 120 may each individually represent a fuzzy set. The forecast data 120 may be determined by a comparison of the degree of match between a first fuzzy set and a second fuzzy set, and/or single values therein with each other or with either set, which is sufficient for purposes of the matching process.

Still referring to FIG. 1, the forecast data 120 may be determined as a function of the intersection between two fuzzy sets. Ranking the forecast data 120 may include utilizing a fuzzy set inference system as described herein below, or any scoring methods as described throughout this disclosure. For example, without limitation processor 104 may use a fuzzy logic model to determine forecast data 120 as a function of fuzzy set comparison techniques as described in this disclosure. In some embodiments, each piece of information associated with a plurality of user data 112 may be compared to one or more examples of forecast data 120, wherein forecast data 120 may be represented using a linguistic variable on a range of potential numerical values, where values for the linguistic variable may be represented as fuzzy sets on that range; a "good" or "ideal" fuzzy set may correspond to a range of values that can be characterized as ideal, while other fuzzy sets may correspond to ranges that can be characterized as mediocre, bad, or other less-than-ideal ranges and/or values. In embodiments, these variables may be used to compare user data 112 and an example of forecast data 120 with a goal of generating forecast data 120 specific to the user profile 108. A fuzzy inferencing system may combine such linguistic variable values according to one or more fuzzy inferencing rules, including any type of fuzzy inferencing system and/or rules as described in this disclosure, to determine a degree of membership in one or more output linguistic variables having values representing ideal overall performance, mediocre or middling overall performance, and/or low or poor overall performance; such mappings may, in turn, be "defuzzified" as described in further detail below to provide an overall output and/or assessment.

Still referring to FIG. 1, the processor may be configured to generate a machine-learning model, such as forecast machine-learning model 128, using a Naïve Bayes classification algorithm. Naïve Bayes classification algorithm generates classifiers by assigning class labels to problem instances, represented as vectors of element values. Class labels are drawn from a finite set. Naïve Bayes classification algorithm may include generating a family of algorithms that assume that the value of a particular element is independent of the value of any other element, given a class variable. Naïve Bayes classification algorithm may be based on Bayes Theorem expressed as $P(A/B)=P(B/A) P(A)\div P(B)$, where $P(A/B)$ is the probability of hypothesis A given data B also known as posterior probability; $P(B/A)$ is the probability of data B given that the hypothesis A was true; $P(A)$ is the probability of hypothesis A being true regardless of data also known as prior probability of A; and $P(B)$ is the probability of the data regardless of the hypothesis. A naïve Bayes algorithm may be generated by first transforming training data into a frequency table. processor 104 may then calculate a likelihood table by calculating probabilities of different data entries and classification labels. processor 104 may utilize a naïve Bayes equation to calculate a posterior probability for each class. A class containing the highest posterior probability is the outcome of prediction. Naïve Bayes classification algorithm may include a gaussian model that follows a normal distribution. Naïve Bayes classification algorithm may include a multinomial model that is used for discrete counts. Naïve Bayes classification algorithm may include a Bernoulli model that may be utilized when vectors are binary.

Still referring to FIG. 1, processor 104 may be configured to generate a machine-learning model, such as forecast machine-learning model 128, using a K-nearest neighbors (KNN) algorithm. A "K-nearest neighbors algorithm" as used in this disclosure, includes a classification method that utilizes feature similarity to analyze how closely out-of-sample-features resemble training data to classify input data to one or more clusters and/or categories of features as represented in training data; this may be performed by representing both training data and input data in vector forms, and using one or more measures of vector similarity to identify classifications within training data, and to determine a classification of input data. K-nearest neighbors algorithm may include specifying a K-value, or a number directing the classifier to select the k most similar entries training data to a given sample, determining the most common classifier of the entries in the database, and classifying the known sample; this may be performed recursively and/or iteratively to generate a classifier that may be used to classify input data as further samples. For instance, an initial set of samples may be performed to cover an initial heuristic and/or "first guess" at an output and/or relationship, which may be seeded, without limitation, using expert input received according to any process as described herein. As a non-limiting example, an initial heuristic may include a ranking of associations between inputs and elements of training data. Heuristic may include selecting some number of highest-ranking associations and/or training data elements.

With continued reference to FIG. 1, generating k-nearest neighbors algorithm may generate a first vector output containing a data entry cluster, generating a second vector output containing an input data, and calculate the distance between the first vector output and the second vector output using any suitable norm such as cosine similarity, Euclidean distance measurement, or the like. Each vector output may be represented, without limitation, as an n-tuple of values, where n is at least two values. Each value of n-tuple of values may represent a measurement or other quantitative value associated with a given category of data, or attribute, examples of which are provided in further detail below; a vector may be represented, without limitation, in n-dimensional space using an axis per category of value represented in n-tuple of values, such that a vector has a geometric direction characterizing the relative quantities of attributes in the n-tuple as compared to each other. Two vectors may be considered equivalent where their directions, and/or the relative quantities of values within each vector as compared to each other, are the same; thus, as a non-limiting example, a vector represented as [5, 10, 15] may be treated as equivalent, for purposes of this disclosure, as a vector represented as [1, 2, 3]. Vectors may be more similar where their directions are more similar, and more different where their directions are more divergent; however, vector similarity may alternatively or additionally be determined using averages of similarities between like attributes, or any other measure of similarity suitable for any n-tuple of values, or aggregation of numerical similarity measures for the purposes of loss functions as described in further detail below. Any vectors as described herein may be scaled, such that each vector represents each attribute along an equivalent scale of values. Each vector may be "normalized," or divided by a "length" attribute, such as a length attribute l as derived using a Pytgoreannorm $l=\sqrt{\Sigma_{i=0}^{n} a_i^2}$, where $a_i$ is attribute number experience of the vector. Scaling and/or normalization may function to make vector comparison independent of absolute quantities of attributes, while preserving any dependency on the similarity of attributes; this may, for instance, be advantageous where cases represented in training data are represented by different quantities of samples, which may result in proportionally equivalent vectors with divergent values.

With continued reference to FIG. 1, processor 104 is configured to generate a plurality of personal targets 132 as a function of the forecast data 120. As used in the current disclosure, a "personal target" is a singular goal of a set of goals used to help the user reach the quality of life predicted by forecast data 120. A personal target 132 may include a plurality of instructions regarding how to achieve the quality of life predicted by forecast data 120. In an embodiment, each personal target 132 of the plurality of personal targets 132 may be associated with a timeline of the users. In a non-limiting example, a processor 104 may be configured to assign a user a personal target 132 for each year until their predicted death a function of tenure data 116. In an embodiment, a personal target 132 may be generated as a function of the selection of the forecast data 120, pecuniary status, lifestyle status, and the like. A personal target 132 may be the quality of life as predicted by the forecast data 120 broken down into a series of sub-targets. In some embodiments, the sub-targets may be smaller more achievable goals used to progress the user toward their desired quality of life. In a non-limiting example, processor 104 generates indicates a pecuniary status 124 the user owning a 20-unit real estate portfolio valued at 4 million dollars. A personal target 132 for the pecuniary status 124 may include buying a property within a calendar year. A personal target 132 may include steps for buying the property such as: 1. conducting an evaluation of the user's credit; 2. identifying a price range; 3. promoting the users to save enough money for a down payment; 4. identifying a property for sale within the price range; 5. Arranging the financing of the property; 6. close on the home. Additionally, personal target 132 may be comprised of a plurality of steps and sub steps. A step may comprise a task that a user must complete in to achieve the desired quality of life. Once a user has achieved a plurality of steps and subs steps the user may achieve a waypoint. In embodiments, a personal target 132 may be comprised of a set of waypoints. As used in the current disclosure, a "waypoint" is a milestone for accomplishing the personal target 132. A non-limiting example of a waypoint may be saving 20% of the total cost of a home for a down payment, in reference to the above example. As used in the current disclosure, a "milestone" is an event marking a significant change or progress for the user achieving his or her personal target 132.

With continued reference to FIG. 1, a personal target may include a health target. As used in the current disclosure, "health target" is a personal target 132 aimed at improving user's health. Examples of health targets may include eliminating or reducing use of illegal substances, improving user's diet, improving the user's level of physical activity, stress reduction, encouraging regular visits to a doctor, and the like. A health target may be aimed at improving a user's health condition data and a health impact factor. In a non-limiting example, a user's lifestyle data indicates a history of substance abuse. The user's substance abuse negatively impacted the user's health condition data and the health impact factor. A health target may include a plan to get the user to end their substance abuse. In another non-limiting example, a user's health condition data may indicate that the user has a high likelihood of getting prostate cancer. Processor 104 may generate a health target for the user of getting his prostate checked yearly.

Still referring to FIG. 1, a personal target 132 may be generated as a function of a user target. As used in the current disclosure, a "user target" is a goal set by the user. A user target be directed toward improving the user's skill, capabilities, past activities, hobbies, interests, and the like. A user target may be extracted from a user via user responses to several questions. This may be done using the chatbot system of FIG. 7. In an embodiment, processor 104 may ask questions about the user's hobbies, activities, current goals, short-term goals, long-term goals, things of interest, and the like. Processor 104 may generate a personal target 132 as a function of a user target using a target synergy process. As used in the current disclosure, the "target synergy process" is a process that incorporates the user target into a set of personal targets 132. In anon limiting example, a user may have a user target of running a marathon. A user may additionally have a health target of losing 65 lbs. Processor 104 may synchronize both of the user's goals using a target synergy process. A target synergy process may include identifying similar sub-goals within each of a personal target 132 and a user goal. In furtherance of the above example, both a health goal and a user goal may require the user to improve their conditioning, thus sub-goals for improving the conditioning of the user may be set. In another non-limiting example, a user may have a personal target 132 to become a millionaire at the age of 45. Additionally, a user may have a user goal of purchasing a home. A target synergy process may include identifying ways a user can improve his or her net worth by purchasing a home. A target synergy process may align a personal target 132 to a user target using a resource vector. A resource vector may be an identification of the skills, materials, time, and experience for a user to accomplish a user goal or/and personal target 132. Processor 104 may be configured to identify any overlap that exists between a resource vector of the user goal and the resource vector of the personal target 132. If the resource vectors align sub-goals may be generated which progresses the user towards both simultaneously.

Still referring to FIG. 1, each personal target 132 of the plurality of personal targets may be assigned a temporal order in which they are accomplished. A "temporal order" is a chronological succession by which each personal target 132 must be accomplished. A temporal order may be determined as a function of the level of difficulty of each personal target 132. A temporal order may be established as a function of resources. In a non-limiting example, if a user has a personal goal 132 of owning a large real estate portfolio by the age of 56. The first personal target 132 of the plurality of personal targets 132 may be to identify, gather, and build the user's monetary resources. A temporal order may be established by ranking a plurality of personal targets 132. In some embodiments, the lower ranked personal target 132 may be done first while higher ranked personal targets 132 subsequently in the order of their ranking. As used in the current disclosure, a "temporal machine-learning model" is a machine-learning model that sorts inputs into categories or bins of data, outputting the categories or bins of data and/or labels associated therewith. The temporal machine-learning model may be consistent with the classifier described below in FIG. 2. Inputs to the temporal machine-learning model may include user profile 108, user data 112, tenure data 116, physiological data, lifestyle data, examples of forecast data 120, pecuniary status, lifestyle status, a plurality of personal targets 132, examples of temporal orders, and the like. Outputs to the temporal machine-learning model may include a temporal order for each personal target of the plurality of personal targets. Temporal training data is a plurality of data entries containing a plurality of inputs that are correlated to a plurality of outputs for training a processor by a machine-learning process to correlate a plurality of personal targets 132 to examples of temporal orders. Temporal training data may be received from database 300. Temporal training data may contain information about user profile 108, user data 112, tenure data 116, physiological data, lifestyle data, examples of forecast data 120, pecuniary status, lifestyle status, a plurality of personal targets 132, examples of temporal orders, and the like. Temporal training data may be configured to correlate the plurality of personal targets 132 to examples of temporal orders. Classification may be performed using, without limitation, linear classifiers such as without limitation logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers.

Still referring to FIG. 1, processor 104 may be configured to display the tenure data 116, forecast data 120, and a personal target 132 using a display device 136. As used in the current disclosure, a "display device" is a device that is used to display a content processor 104. A display device 136 may include a user interface. A "user interface," as used herein, is a means by which a user and a computer system interact; for example through the use of input devices and software. A user interface may include a graphical user interface (GUI), command line interface (CLI), menu-driven user interface, touch user interface, voice user interface (VUI), form-based user interface, any combination thereof, and the like. A user interface may include a smartphone, smart tablet, desktop, or laptop operated by the user. In an embodiment, the user interface may include a graphical user interface. A "graphical user interface (GUI)," as used herein, is a graphical form of user interface that allows users to interact with electronic devices. In some embodiments, GUI may include icons, menus, other visual indicators, or representations (graphics), audio indicators such as primary notation, and display information and related user controls. A menu may contain a list of choices and may allow users to select one from them. A menu bar may be displayed horizontally across the screen such as pull down menu. When any option is clicked in this menu, then the pull down menu may appear. A menu may include a context menu that appears only when the user performs a specific action. An example of this is pressing the right mouse button. When this is done, a menu may appear under the cursor. Files, programs, web pages and the like may be represented using a small picture in a graphical user interface. For example, links to decentralized platforms as described in this disclosure may be incorporated using icons. Using an icon may be a fast way to open documents, run programs etc. because clicking on them yields instant access. Information contained in user interface may be directly influenced using graphical control elements such as widgets. A "widget," as used herein, is a user control element that allows a user to control and change the appearance of elements in the user interface. In this context a widget may refer to a generic GUI element such as a check box, button, or scroll bar to an instance of that element, or to a customized collection of such elements used for a specific function or application (such as a dialog box for users to customize their computer screen appearances). User interface controls may include software components that a user interacts with through direct manipulation to read or edit information displayed through user interface. Widgets may be used to display lists of related items, navigate the system using links, tabs, and manipulate data using check boxes, radio boxes, and the like.

Figure 2:
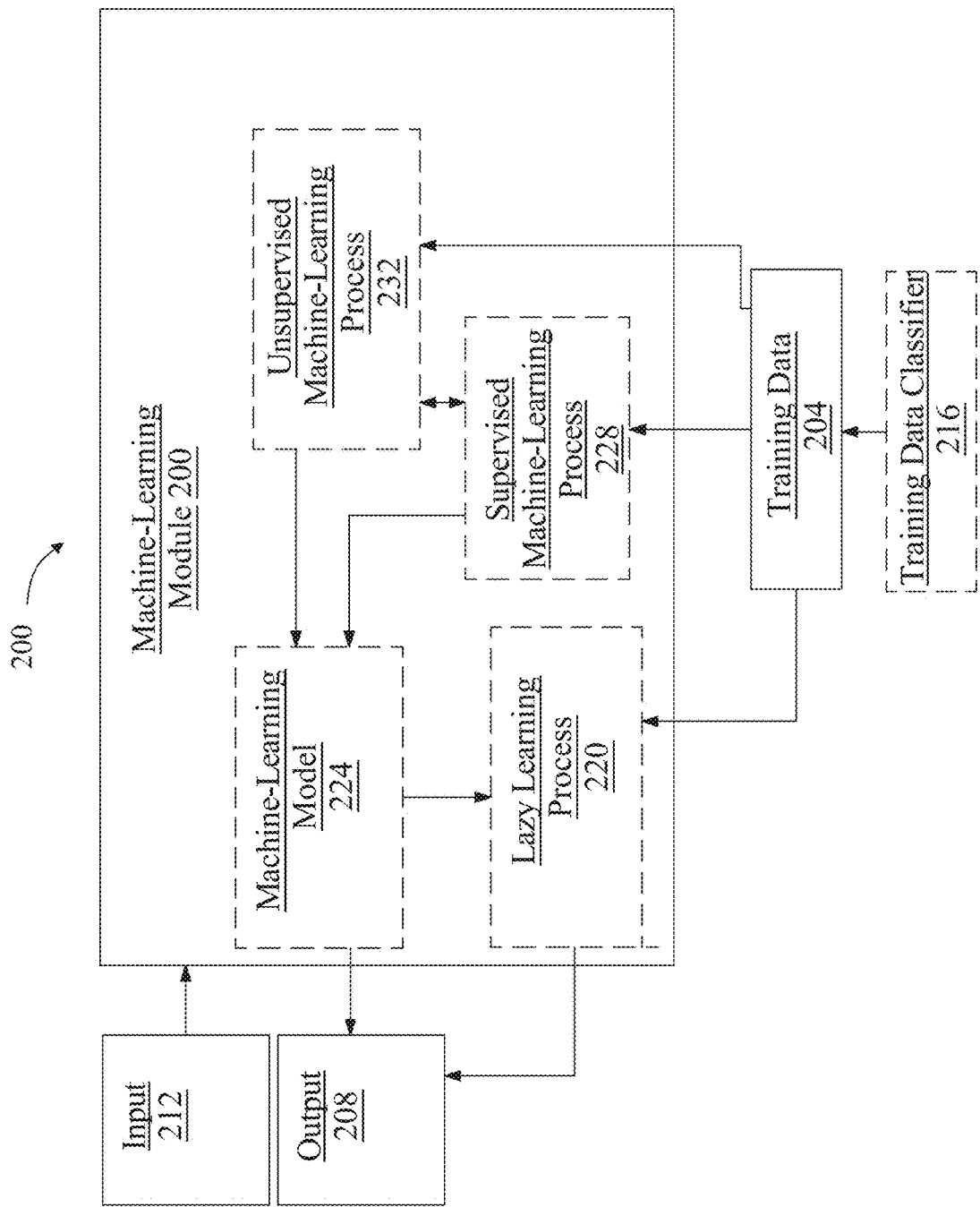
FIG. 2 is a block diagram of an exemplary machine-learning process.

Referring now to FIG. 2, an exemplary embodiment of a machine-learning module 200 that may perform one or more machine-learning processes as described in this disclosure is illustrated. Machine-learning modules may perform determinations, classification, and/or analysis steps, methods, processes, or the like as described in this disclosure using machine-learning processes. A "machine learning process," as used in this disclosure, is a process that automatedly uses training data 204 to generate an algorithm that will be performed by a computing device/module to produce outputs 208 given data provided as inputs 212; this is in contrast to a non-machine learning software program where the commands to be executed are determined in advance by a user and written in a programming language.

Still referring to FIG. 2, "training data," as used herein, is data containing correlations that a machine-learning process may use to model relationships between two or more categories of data elements. For instance, and without limitation, training data 204 may include a plurality of data entries, each entry representing a set of data elements that were recorded, received, and/or generated together; data elements may be correlated by shared existence in a given data entry, by proximity in a given data entry, or the like. Multiple data entries in training data 204 may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data 204 according to various correlations; correlations may indicate causative and/or predictive links between categories of data elements, which may be modeled as relationships such as mathematical relationships by machine-learning processes as described in further detail below. Training data 204 may be formatted and/or organized by categories of data elements, for instance by associating data elements with one or more descriptors corresponding to categories of data elements. As a non-limiting example, training data 204 may include data entered in standardized forms by persons or processes, such that entry of a given data element in a given field in a form may be mapped to one or more descriptors of categories. Elements in training data 204 may be linked to descriptors of categories by tags, tokens, or other data elements; for instance, and without limitation, training data 204 may be provided in fixed-length formats, formats linking positions of data to categories such as comma-separated value (CSV) formats and/or self-describing formats such as extensible markup language (XML), JavaScript Object Notation (JSON), or the like, enabling processes or devices to detect categories of data.

Alternatively or additionally, and continuing to refer to FIG. 2, training data 204 may include one or more elements that are not categorized; that is, training data 204 may not be formatted or contain descriptors for some elements of data. Machine-learning algorithms and/or other processes may sort training data 204 according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name may be identified by reference to a list, dictionary, or other compendium of terms, permitting ad-hoc categorization by machine-learning algorithms, and/or automated association of data in the data entry with descriptors or into a given format. The ability to categorize data entries automatedly may enable the same training data 204 to be made applicable for two or more distinct machine-learning algorithms as described in further detail below. Training data 204 used by machine-learning module 200 may correlate any input data as described in this disclosure to any output data as described in this disclosure.

Further referring to FIG. 2, training data may be filtered, sorted, and/or selected using one or more supervised and/or unsupervised machine-learning processes and/or models as described in further detail below; such models may include without limitation a training data classifier 216. Training data classifier 216 may include a "classifier," which as used in this disclosure is a machine-learning model as defined below, such as a mathematical model, neural net, or program generated by a machine learning algorithm known as a "classification algorithm," as described in further detail below, that sorts inputs into categories or bins of data, outputting the categories or bins of data and/or labels associated therewith. A classifier may be configured to output at least a datum that labels or otherwise identifies a set of data that are clustered together, found to be close under a distance metric as described below, or the like. Machine-learning module 200 may generate a classifier using a classification algorithm, defined as a processes whereby a computing device and/or any module and/or component operating thereon derives a classifier from training data 204. Classification may be performed using, without limitation, linear classifiers such as without limitation logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers.

Still referring to FIG. 2, machine-learning module 200 may be configured to perform a lazy-learning process 220 and/or protocol, which may alternatively be referred to as a "lazy loading" or "call-when-needed" process and/or protocol, maybe a process whereby machine learning is conducted upon receipt of an input to be converted to an output, by combining the input and training set to derive the algorithm to be used to produce the output on demand. For instance, an initial set of simulations may be performed to cover an initial heuristic and/or "first guess" at an output and/or relationship. As a non-limiting example, an initial heuristic may include a ranking of associations between inputs and elements of training data 204. Heuristic may include selecting some number of highest-ranking associations and/or training data 204 elements. Lazy learning may implement any suitable lazy learning algorithm, including without limitation a K-nearest neighbors algorithm, a lazy naïve Bayes algorithm, or the like; persons skilled in the art, upon reviewing the entirety of this disclosure, will be aware of various lazy-learning algorithms that may be applied to generate outputs as described in this disclosure, including without limitation lazy learning applications of machine-learning algorithms as described in further detail below.

Alternatively or additionally, and with continued reference to FIG. 2, machine-learning processes as described in this disclosure may be used to generate machine-learning models 224. A "machine-learning model," as used in this disclosure, is a mathematical and/or algorithmic representation of a relationship between inputs and outputs, as generated using any machine-learning process including without limitation any process as described above, and stored in memory; an input is submitted to a machine-learning model 224 once created, which generates an output based on the relationship that was derived. For instance, and without limitation, a linear regression model, generated using a linear regression algorithm, may compute a linear combination of input data using coefficients derived during machine-learning processes to calculate an output datum. As a further non-limiting example, a machine-learning model 224 may be generated by creating an artificial neural network, such as a convolutional neural network comprising an input layer of nodes, one or more intermediate layers, and an output layer of nodes. Connections between nodes may be created via the process of "training" the network, in which elements from a training data 204 set are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning.

Still referring to FIG. 2, machine-learning algorithms may include at least a supervised machine-learning process 228. At least a supervised machine-learning process 228, as defined herein, include algorithms that receive a training set relating a number of inputs to a number of outputs, and seek to find one or more mathematical relations relating inputs to outputs, where each of the one or more mathematical relations is optimal according to some criterion specified to the algorithm using some scoring function. For instance, a supervised learning algorithm may include inputs and outputs as described above in this disclosure, and a scoring function representing a desired form of relationship to be detected between inputs and outputs; scoring function may, for instance, seek to maximize the probability that a given input and/or combination of elements inputs is associated with a given output to minimize the probability that a given input is not associated with a given output. Scoring function may be expressed as a risk function representing an "expected loss" of an algorithm relating inputs to outputs, where loss is computed as an error function representing a degree to which a prediction generated by the relation is incorrect when compared to a given input-output pair provided in training data 204. Persons skilled in the art, upon reviewing the entirety of this disclosure, will be aware of various possible variations of at least a supervised machine-learning process 228 that may be used to determine relation between inputs and outputs. Supervised machine-learning processes may include classification algorithms as defined above.

Further referring to FIG. 2, machine learning processes may include at least an unsupervised machine-learning processes 232. An unsupervised machine-learning process, as used herein, is a process that derives inferences in datasets without regard to labels; as a result, an unsupervised machine-learning process may be free to discover any structure, relationship, and/or correlation provided in the data. Unsupervised processes may not require a response variable; unsupervised processes may be used to find interesting patterns and/or inferences between variables, to determine a degree of correlation between two or more variables, or the like.

Still referring to FIG. 2, machine-learning module 200 may be designed and configured to create a machine-learning model 224 using techniques for development of linear regression models. Linear regression models may include ordinary least squares regression, which aims to minimize the square of the difference between predicted outcomes and actual outcomes according to an appropriate norm for measuring such a difference (e.g. a vector-space distance norm); coefficients of the resulting linear equation may be modified to improve minimization. Linear regression models may include ridge regression methods, where the function to be minimized includes the least-squares function plus term multiplying the square of each coefficient by a scalar amount to penalize large coefficients. Linear regression models may include least absolute shrinkage and selection operator (LASSO) models, in which ridge regression is combined with multiplying the least-squares term by a factor of 1 divided by double the number of samples. Linear regression models may include a multi-task lasso model wherein the norm applied in the least-squares term of the lasso model is the Frobenius norm amounting to the square root of the sum of squares of all terms. Linear regression models may include the elastic net model, a multi-task elastic net model, a least angle regression model, a LARS lasso model, an orthogonal matching pursuit model, a Bayesian regression model, a logistic regression model, a stochastic gradient descent model, a perceptron model, a passive aggressive algorithm, a robustness regression model, a Huber regression model, or any other suitable model that may occur to persons skilled in the art upon reviewing the entirety of this disclosure. Linear regression models may be generalized in an embodiment to polynomial regression models, whereby a polynomial equation (e.g. a quadratic, cubic or higher-order equation) providing a best predicted output/actual output fit is sought; similar methods to those described above may be applied to minimize error functions, as will be apparent to persons skilled in the art upon reviewing the entirety of this disclosure.

Continuing to refer to FIG. 2, machine-learning algorithms may include, without limitation, linear discriminant analysis. Machine-learning algorithm may include quadratic discriminate analysis. Machine-learning algorithms may include kernel ridge regression. Machine-learning algorithms may include support vector machines, including without limitation support vector classification-based regression processes. Machine-learning algorithms may include stochastic gradient descent algorithms, including classification and regression algorithms based on stochastic gradient descent. Machine-learning algorithms may include nearest neighbors algorithms. Machine-learning algorithms may include various forms of latent space regularization such as variational regularization. Machine-learning algorithms may include Gaussian processes such as Gaussian Process Regression. Machine-learning algorithms may include cross-decomposition algorithms, including partial least squares and/or canonical correlation analysis. Machine-learning algorithms may include naïve Bayes methods. Machine-learning algorithms may include algorithms based on decision trees, such as decision tree classification or regression algorithms. Machine-learning algorithms may include ensemble methods such as bagging meta-estimator, forest of randomized tress, AdaBoost, gradient tree boosting, and/or voting classifier methods. Machine-learning algorithms may include neural net algorithms, including convolutional neural net processes.

Figure 3:
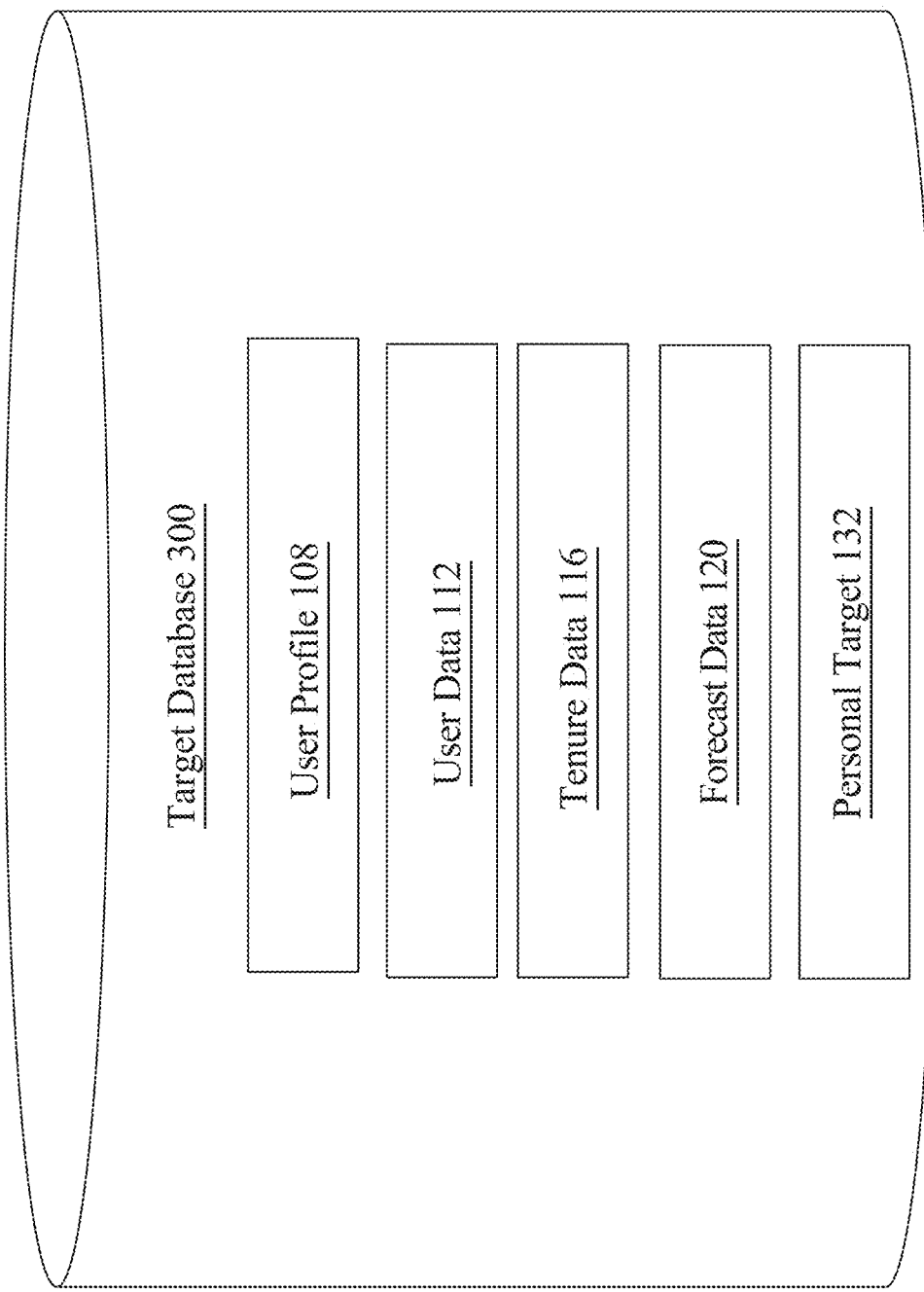
FIG. 3 is a block diagram of an exemplary embodiment of a target database.

Now referring to FIG. 3, an exemplary target database 300 is illustrated by way of block diagram. In an embodiment, any past or present versions of data disclosed herein may be stored within user profile 108, user data 112, tenure data 116, forecast data 120, pecuniary status 124, personal target 132, and the like. Processor 104 may be communicatively connected with target database 300. For example, in some cases, database 300 may be local to processor 104. Alternatively or additionally, in some cases, database 300 may be remote to processor 104 and communicative with processor 104 by way of one or more networks. Network may include, but not limited to, a cloud network, a mesh network, or the like. By way of example, a "cloud-based" system, as that term is used herein, can refer to a system which includes software and/or data which is stored, managed, and/or processed on a network of remote servers hosted in the "cloud," e.g., via the Internet, rather than on local severs or personal computers. A "mesh network" as used in this disclosure is a local network topology in which the infrastructure processor 104 connect directly, dynamically, and non-hierarchically to as many other computing devices as possible. A "network topology" as used in this disclosure is an arrangement of elements of a communication network. Target database 300 may be implemented, without limitation, as a relational database, a key-value retrieval database such as a NOSQL database, or any other format or structure for use as a database that a person skilled in the art would recognize as suitable upon review of the entirety of this disclosure. Target database 300 may alternatively or additionally be implemented using a distributed data storage protocol and/or data structure, such as a distributed hash table or the like. Target database 300 may include a plurality of data entries and/or records as described above. Data entries in a database may be flagged with or linked to one or more additional elements of information, which may be reflected in data entry cells and/or in linked tables such as tables related by one or more indices in a relational database. Persons skilled in the art, upon reviewing the entirety of this disclosure, will be aware of various ways in which data entries in a database may store, retrieve, organize, and/or reflect data and/or records as used herein, as well as categories and/or populations of data consistently with this disclosure.

Figure 4:
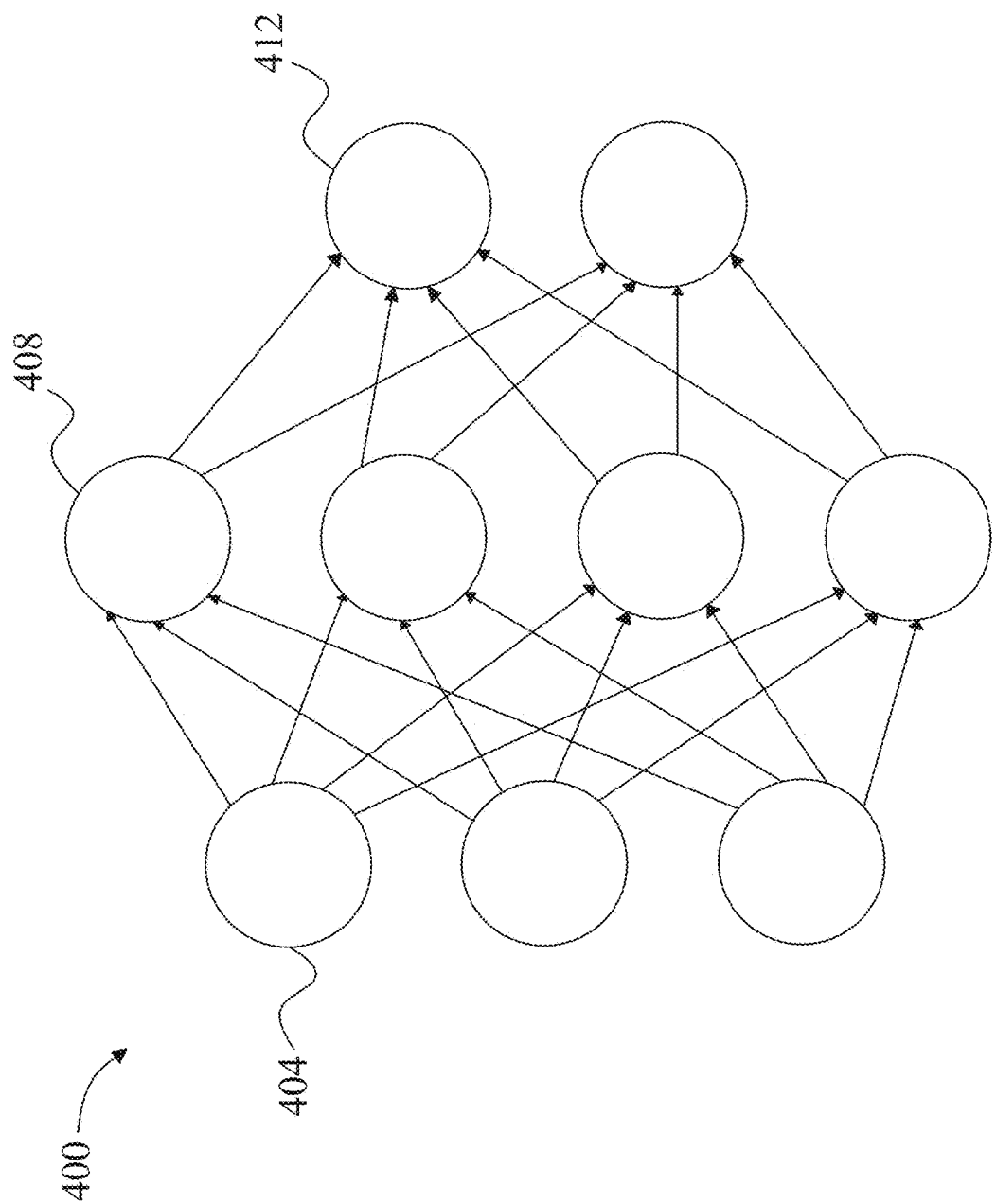
FIG. 4 is a diagram of an exemplary embodiment of a neural network.

Referring now to FIG. 4, an exemplary embodiment of neural network 400 is illustrated. A neural network 400 also known as an artificial neural network, is a network of "nodes," or data structures having one or more inputs, one or more outputs, and a function determining outputs based on inputs. Such nodes may be organized in a network, such as without limitation a convolutional neural network, including an input layer of nodes 404, one or more intermediate layers 408, and an output layer of nodes 412. Connections between nodes may be created via the process of "training" the network, in which elements from a training dataset are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning. Connections may run solely from input nodes toward output nodes in a "feed-forward" network or may feed outputs of one layer back to inputs of the same or a different layer in a "recurrent network." As a further non-limiting example, a neural network may include a convolutional neural network comprising an input layer of nodes, one or more intermediate layers, and an output layer of nodes. A "convolutional neural network," as used in this disclosure, is a neural network in which at least one hidden layer is a convolutional layer that convolves inputs to that layer with a subset of inputs known as a "kernel," along with one or more additional layers such as pooling layers, fully connected layers, and the like.

Figure 5:
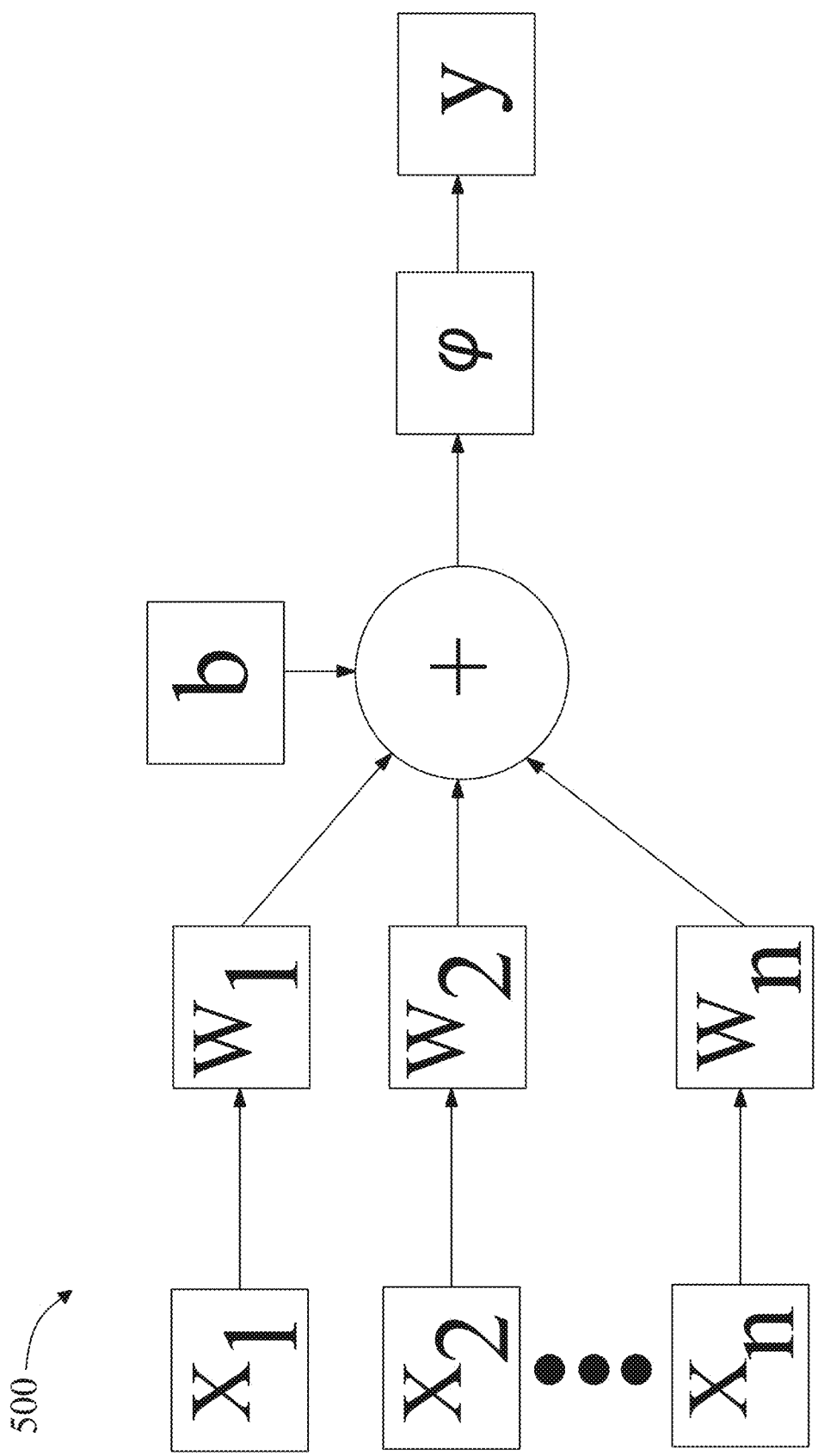
FIG. 5 is a diagram of an exemplary embodiment of a node of a neural network.

Referring now to FIG. 5, an exemplary embodiment of a node of a neural network is illustrated. A node may include, without limitation, a plurality of inputs $x_i$ that may receive numerical values from inputs to a neural network containing the node and/or from other nodes. Node may perform a weighted sum of inputs using weights $w_i$ that are multiplied by respective inputs $x_i$. Additionally or alternatively, a bias b may be added to the weighted sum of the inputs such that an offset is added to each unit in the neural network layer that is independent of the input to the layer. The weighted sum may then be input into a function $\varphi$, which may generate one or more outputs y. Weight $w_i$ applied to an input $x_i$ may indicate whether the input is "excitatory," indicating that it has strong influence on the one or more outputs y, for instance by the corresponding weight having a large numerical value, and/or a "inhibitory," indicating it has a weak effect influence on the one more inputs y, for instance by the corresponding weight having a small numerical value. The values of weights $w_i$ may be determined by training a neural network using training data, which may be performed using any suitable process as described above.

Figure 6:
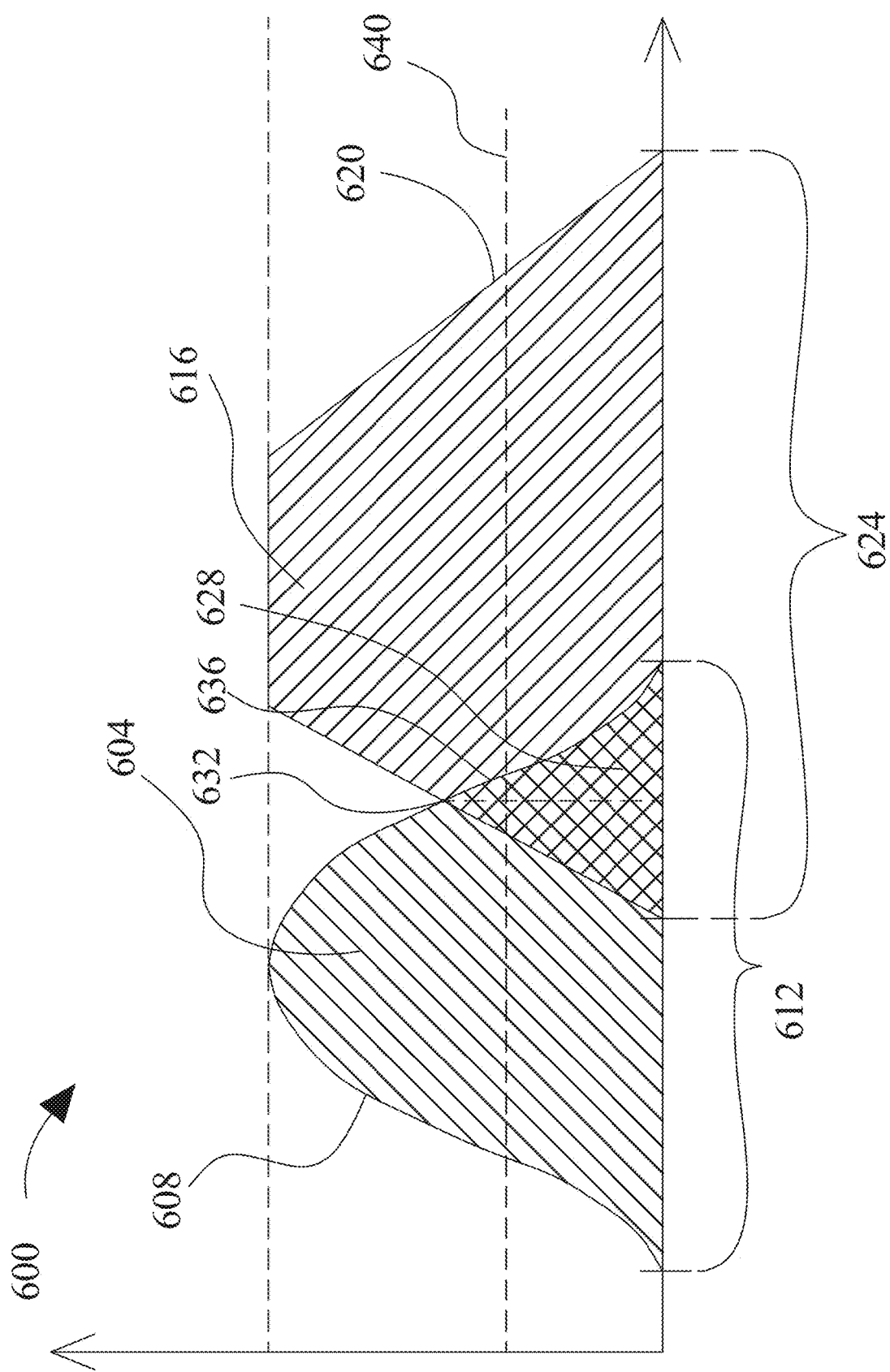
FIG. 6 an illustration exemplary embodiment of fuzzy set comparison.

Now referring to FIG. 6, an exemplary embodiment of fuzzy set comparison 600 is illustrated. In a non-limiting embodiment, the fuzzy set comparison. In a non-limiting embodiment, fuzzy set comparison 600 may be consistent with fuzzy set comparison in FIG. 1. In another non-limiting the fuzzy set comparison 600 may be consistent with the name/version matching as described herein. For example and without limitation, the parameters, weights, and/or coefficients of the membership functions may be tuned using any machine-learning methods for the name/version matching as described herein. In another non-limiting embodiment, the fuzzy set may represent a plurality of user data 112 and an example of a forecast data 120 from FIG. 1.

Alternatively or additionally, and still referring to FIG. 6, fuzzy set comparison 600 may be generated as a function of determining data compatibility threshold. The compatibility threshold may be determined by a computing device. In some embodiments, a computing device may use a logic comparison program, such as, but not limited to, a fuzzy logic model to determine the compatibility threshold and/or version authenticator. Each such compatibility threshold may be represented as a value for a posting variable representing the compatibility threshold, or in other words a fuzzy set as described above that corresponds to a degree of compatibility and/or allowability as calculated using any statistical, machine-learning, or other method that may occur to a person skilled in the art upon reviewing the entirety of this disclosure. In some embodiments, determining the compatibility threshold and/or version authenticator may include using a linear regression model. A linear regression model may include a machine learning model. A linear regression model may map statistics such as, but not limited to, frequency of the same range of version numbers, and the like, to the compatibility threshold and/or version authenticator. In some embodiments, determining the compatibility threshold of any posting may include using a classification model. A classification model may be configured to input collected data and cluster data to a centroid based on, but not limited to, frequency of appearance of the range of versioning numbers, linguistic indicators of compatibility and/or allowability, and the like. Centroids may include scores assigned to them such that the compatibility threshold may each be assigned a score. In some embodiments, a classification model may include a K-means clustering model. In some embodiments, a classification model may include a particle swarm optimization model. In some embodiments, determining a compatibility threshold may include using a fuzzy inference engine. A fuzzy inference engine may be configured to map one or more compatibility threshold using fuzzy logic. In some embodiments, a plurality of computing devices may be arranged by a logic comparison program into compatibility arrangements. A "compatibility arrangement" as used in this disclosure is any grouping of objects and/or data based on skill level and/or output score. Membership function coefficients and/or constants as described above may be tuned according to classification and/or clustering algorithms. For instance, and without limitation, a clustering algorithm may determine a Gaussian or other distribution of questions about a centroid corresponding to a given compatibility threshold and/or version authenticator, and an iterative or other method may be used to find a membership function, for any membership function type as described above, that minimizes an average error from the statistically determined distribution, such that, for instance, a triangular or Gaussian membership function about a centroid representing a center of the distribution that most closely matches the distribution. Error functions to be minimized, and/or methods of minimization, may be performed without limitation according to any error function and/or error function minimization process and/or method as described in this disclosure.

Still referring to FIG. 6, inference engine may be implemented according to input a plurality of user data 112 and an example of forecast data 120. For instance, an acceptance variable may represent a first measurable value pertaining to the classification of a plurality of user data 112 to an example of forecast data 120. Continuing the example, an output variable may represent an forecast data 120 tailored to the user profile 108. In an embodiment, a plurality of user data 112 and/or an example of forecast data 120 may be represented by their own fuzzy set. In other embodiments, an evaluation factor may be represented as a function of the intersection two fuzzy sets as shown in FIG. 6, An inference engine may combine rules, such as any semantic versioning, semantic language, version ranges, and the like thereof. The degree to which a given input function membership matches a given rule may be determined by a triangular norm or "T-norm" of the rule or output function with the input function, such as min (a, b), product of a and b, drastic product of a and b, Hamacher product of a and b, or the like, satisfying the rules of commutativity (T(a, b)=T(b, a)), monotonicity: (T(a, b)≤T(c, d) if a≤c and b≤d), (associativity: T(a, T(b, c))=T(T (a, b), c)), and the requirement that the number 1 acts as an identity element. Combinations of rules ("and" or "or" combination of rule membership determinations) may be performed using any T-conorm, as represented by an inverted T symbol or "⊥," such as max (a, b), probabilistic sum of a and b (a+b−a*b), bounded sum, and/or drastic T-conorm; any T-conorm may be used that satisfies the properties of commutativity: ⊥(a, b)=⊥(b, a), monotonicity: ⊥(a, b)≤⊥(c, d) if a≤c and b≤d, associativity: ⊥(a, ⊥(b, c))=⊥(⊥(a, b), c), and identity element of 0. Alternatively or additionally T-conorm may be approximated by sum, as in a "product-sum" inference engine in which T-norm is product and T-conorm is sum. A final output score or other fuzzy inference output may be determined from an output membership function as described above using any suitable defuzzification process, including without limitation Mean of Max defuzzification, Centroid of Area/Center of Gravity defuzzification, Center Average defuzzification, Bisector of Area defuzzification, or the like. Alternatively or additionally, output rules may be replaced with functions according to the Takagi-Sugeno-King (TSK) fuzzy model.

A first fuzzy set 604 may be represented, without limitation, according to a first membership function 608 representing a probability that an input falling on a first range of values 612 is a member of the first fuzzy set 604, where the first membership function 608 has values on a range of probabilities such as without limitation the interval [0,1], and an area beneath the first membership function 608 may represent a set of values within first fuzzy set 604. Although first range of values 612 is illustrated for clarity in this exemplary depiction as a range on a single number line or axis, first range of values 612 may be defined on two or more dimensions, representing, for instance, a Cartesian product between a plurality of ranges, curves, axes, spaces, dimensions, or the like. First membership function 608 may include any suitable function mapping first range 612 to a probability interval, including without limitation a triangular function defined by two linear elements such as line segments or planes that intersect at or below the top of the probability interval. As a non-limiting example, triangular membership function may be defined as:

$$y(x, a, b, c) = \begin{cases} 0, & \text{for } x > c \text{ and } x < a \\ \frac{x-a}{b-a}, & \text{for } a \le x < b \\ \frac{c-x}{c-b}, & \text{if } b < x \le c \end{cases}$$

a trapezoidal membership function may be defined as:

$$y(x, a, b, c, d) = \max\left(\min\left(\frac{x-a}{b-a}, 1, \frac{d-x}{d-c}\right), 0\right)$$

a sigmoidal function may be defined as:

$$y(x, a, c) = \frac{1}{1 - e^{-a(x-c)}}$$

a Gaussian membership function may be defined as:

$$y(x, c, \sigma) = e^{-\frac{1}{2}\left(\frac{x-c}{\sigma}\right)^2}$$

and a bell membership function may be defined as:

$$y(x, a, b, c,) = \left[1 + \left|\frac{x-c}{a}\right|^{2b}\right]^{-1}$$

Persons skilled in the art, upon reviewing the entirety of this disclosure, will be aware of various alternative or additional membership functions that may be used consistently with this disclosure.

First fuzzy set 604 may represent any value or combination of values as described above, including any a plurality of user data 112 and an example of forecast data 120. A second fuzzy set 616, which may represent any value which may be represented by first fuzzy set 604, may be defined by a second membership function 620 on a second range 624; second range 624 may be identical and/or overlap with first range 612 and/or may be combined with first range via Cartesian product or the like to generate a mapping permitting evaluation overlap of first fuzzy set 604 and second fuzzy set 616. Where first fuzzy set 604 and second fuzzy set 616 have a region 636 that overlaps, first membership function 608 and second membership function 620 may intersect at a point 632 representing a probability, as defined on probability interval, of a match between first fuzzy set 604 and second fuzzy set 616. Alternatively or additionally, a single value of first and/or second fuzzy set may be located at a locus 636 on first range 612 and/or second range 624, where a probability of membership may be taken by evaluation of first membership function 608 and/or second membership function 620 at that range point. A probability at 628 and/or 632 may be compared to a threshold 640 to determine whether a positive match is indicated. Threshold 640 may, in a non-limiting example, represent a degree of match between first fuzzy set 604 and second fuzzy set 616, and/or single values therein with each other or with either set, which is sufficient for purposes of the matching process; for instance, a forecast data 120 may indicate a sufficient degree of overlap with fuzzy set representing a plurality of user data 112 and an example of forecast data 120 for combination to occur as described above. Each threshold may be established by one or more user inputs. Alternatively or additionally, each threshold may be tuned by a machine-learning and/or statistical process, for instance and without limitation as described in further detail below.

In an embodiment, a degree of match between fuzzy sets may be used to rank one resource against another. For instance, if both a plurality of user data 112 and an example of forecast data 120 have fuzzy sets, an forecast data 120 may be generated by having a degree of overlap exceeding a predictive threshold, processor 104 may further rank the two resources by ranking a resource having a higher degree of match more highly than a resource having a lower degree of match. Where multiple fuzzy matches are performed, degrees of match for each respective fuzzy set may be computed and aggregated through, for instance, addition, averaging, or the like, to determine an overall degree of match, which may be used to rank resources; selection between two or more matching resources may be performed by selection of a highest-ranking resource, and/or multiple notifications may be presented to a user in order of ranking.

Figure 7:
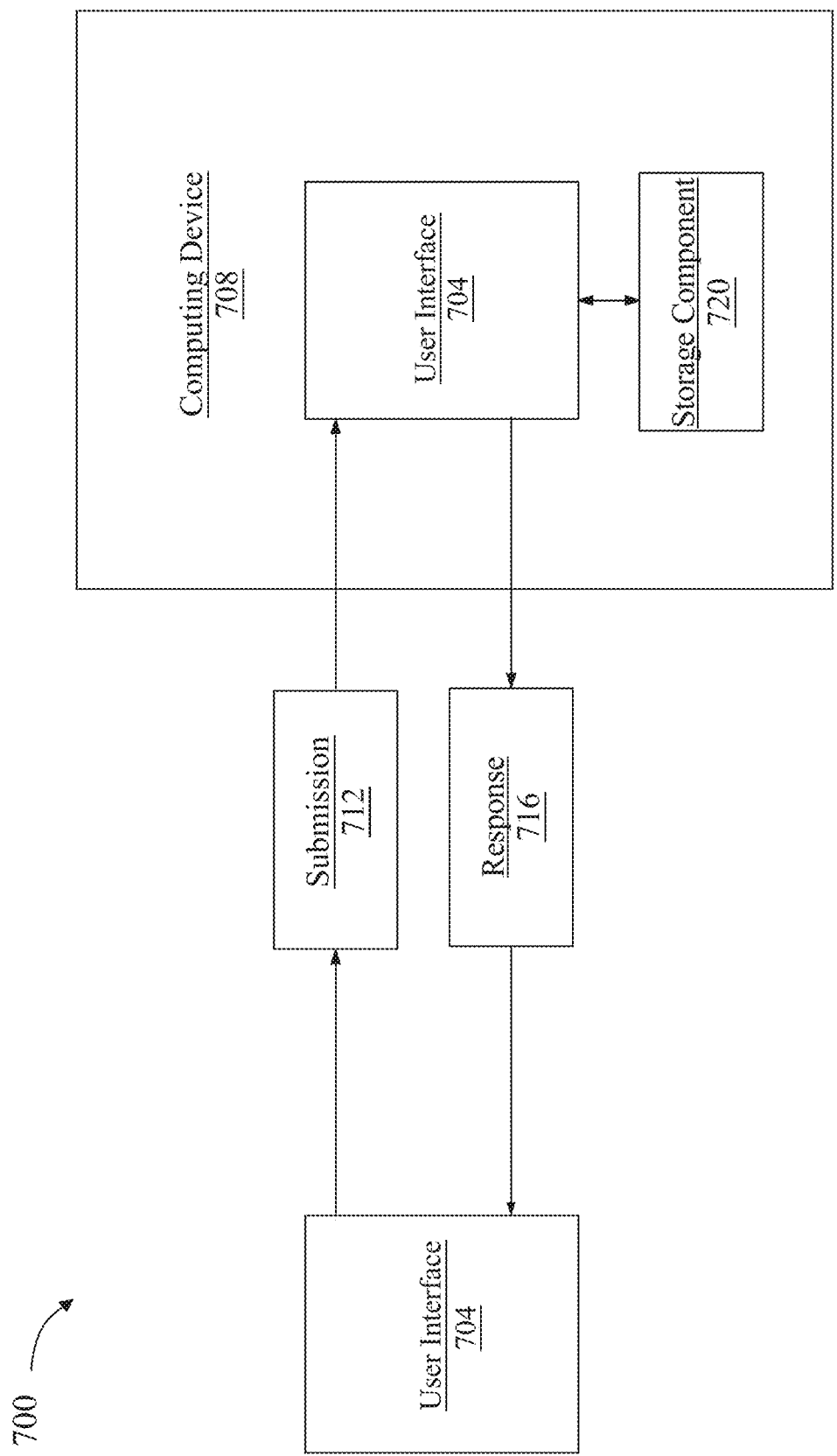
FIG. 7 is an illustration of an exemplary embodiment of a chatbot.

Referring to FIG. 7, a chatbot system 700 is schematically illustrated. According to some embodiments, a user interface 704 may be communicative with a computing device 708 that is configured to operate a chatbot. In some cases, user interface 704 may be local to computing device 708. Alternatively or additionally, in some cases, user interface 704 may remote to computing device 708 and communicative with the computing device 708, by way of one or more networks, such as without limitation the internet. Alternatively or additionally, user interface 704 may communicate with user device 708 using telephonic devices and networks, such as without limitation fax machines, short message service (SMS), or multimedia message service (MMS). Commonly, user interface 704 communicates with computing device 708 using text-based communication, for example without limitation using a character encoding protocol, such as American Standard for Information Interchange (ASCII). Typically, a user interface 704 conversationally interfaces a chatbot, by way of at least a submission 712, from the user interface 708 to the chatbot, and a response 716, from the chatbot to the user interface 704. In many cases, one or both of submission 712 and response 716 are text-based communication. Alternatively or additionally, in some cases, one or both of submission 712 and response 716 are audio-based communication.

Continuing in reference to FIG. 7, a submission 712 once received by computing device 708 operating a chatbot, may be processed by a processor. In some embodiments, processor processes a submission 7112 using one or more of keyword recognition, pattern matching, and natural language processing. In some embodiments, processor employs real-time learning with evolutionary algorithms. In some cases, processor may retrieve a pre-prepared response from at least a storage component 720, based upon submission 712. Alternatively or additionally, in some embodiments, processor communicates a response 716 without first receiving a submission 712, thereby initiating conversation. In some cases, processor communicates an inquiry to user interface 704; and the processor is configured to process an answer to the inquiry in a following submission 712 from the user interface 704. In some cases, an answer to an inquiry present within a submission 712 from a user device 704 may be used by computing device 708 as an input to another function.

With continued reference to FIG. 7, A chatbot may be configured to provide a user with a plurality of options as an input into the chatbot. Chatbot entries may include multiple choice, short answer response, true or false responses, and the like. A user may decide on what type of chatbot entries are appropriate. In some embodiments, the chatbot may be configured to allow the user to input a freeform response into the chatbot. The chatbot may then use a decision tree, data base, or other data structure to respond to the users entry into the chatbot as a function of a chatbot input. As used in the current disclosure, "Chatbot input" is any response that a candidate or employer inputs in to a chatbot as a response to a prompt or question.

With continuing reference to FIG. 7, computing device 708 may be configured to the respond to a chatbot input using a decision tree. A "decision tree," as used in this disclosure, is a data structure that represents and combines one or more determinations or other computations based on and/or concerning data provided thereto, as well as earlier such determinations or calculations, as nodes of a tree data structure where inputs of some nodes are connected to outputs of others. Decision tree may have at least a root node, or node that receives data input to the decision tree, corresponding to at least a candidate input into a chatbot. Decision tree has at least a terminal node, which may alternatively or additionally be referred to herein as a "leaf node," corresponding to at least an exit indication; in other words, decision and/or determinations produced by decision tree may be output at the at least a terminal node. Decision tree may include one or more internal nodes, defined as nodes connecting outputs of root nodes to inputs of terminal nodes. Computing device 708 may generate two or more decision trees, which may overlap; for instance, a root node of one tree may connect to and/or receive output from one or more terminal nodes of another tree, intermediate nodes of one tree may be shared with another tree, or the like.

Still referring to FIG. 7, computing device 708 may build decision tree by following relational identification; for example, relational indication may specify that a first rule module receives an input from at least a second rule module and generates an output to at least a third rule module, and so forth, which may indicate to computing device 708 an in which such rule modules will be placed in decision tree. Building decision tree may include recursively performing mapping of execution results output by one tree and/or subtree to root nodes of another tree and/or subtree, for instance by using such execution results as execution parameters of a subtree. In this manner, computing device 708 may generate connections and/or combinations of one or more trees to one another to define overlaps and/or combinations into larger trees and/or combinations thereof. Such connections and/or combinations may be displayed by visual interface to user, for instance in first view, to enable viewing, editing, selection, and/or deletion by user; connections and/or combinations generated thereby may be highlighted, for instance using a different color, a label, and/or other form of emphasis aiding in identification by a user. In some embodiments, subtrees, previously constructed trees, and/or entire data structures may be represented and/or converted to rule modules, with graphical models representing them, and which may then be used in further iterations or steps of generation of decision tree and/or data structure. Alternatively or additionally subtrees, previously constructed trees, and/or entire data structures may be converted to APIs to interface with further iterations or steps of methods as described in this disclosure. As a further example, such subtrees, previously constructed trees, and/or entire data structures may become remote resources to which further iterations or steps of data structures and/or decision trees may transmit data and from which further iterations or steps of generation of data structure receive data, for instance as part of a decision in a given decision tree node.

Continuing to refer to FIG. 7, decision tree may incorporate one or more manually entered or otherwise provided decision criteria. Decision tree may incorporate one or more decision criteria using an application programmer interface (API). Decision tree may establish a link to a remote decision module, device, system, or the like. Decision tree may perform one or more database lookups and/or look-up table lookups. Decision tree may include at least a decision calculation module, which may be imported via an API, by incorporation of a program module in source code, executable, or other form, and/or linked to a given node by establishing a communication interface with one or more exterior processes, programs, systems, remote devices, or the like; for instance, where a user operating system has a previously existent calculation and/or decision engine configured to make a decision corresponding to a given node, for instance and without limitation using one or more elements of domain knowledge, by receiving an input and producing an output representing a decision, a node may be configured to provide data to the input and receive the output representing the decision, based upon which the node may perform its decision.

Figure 8:
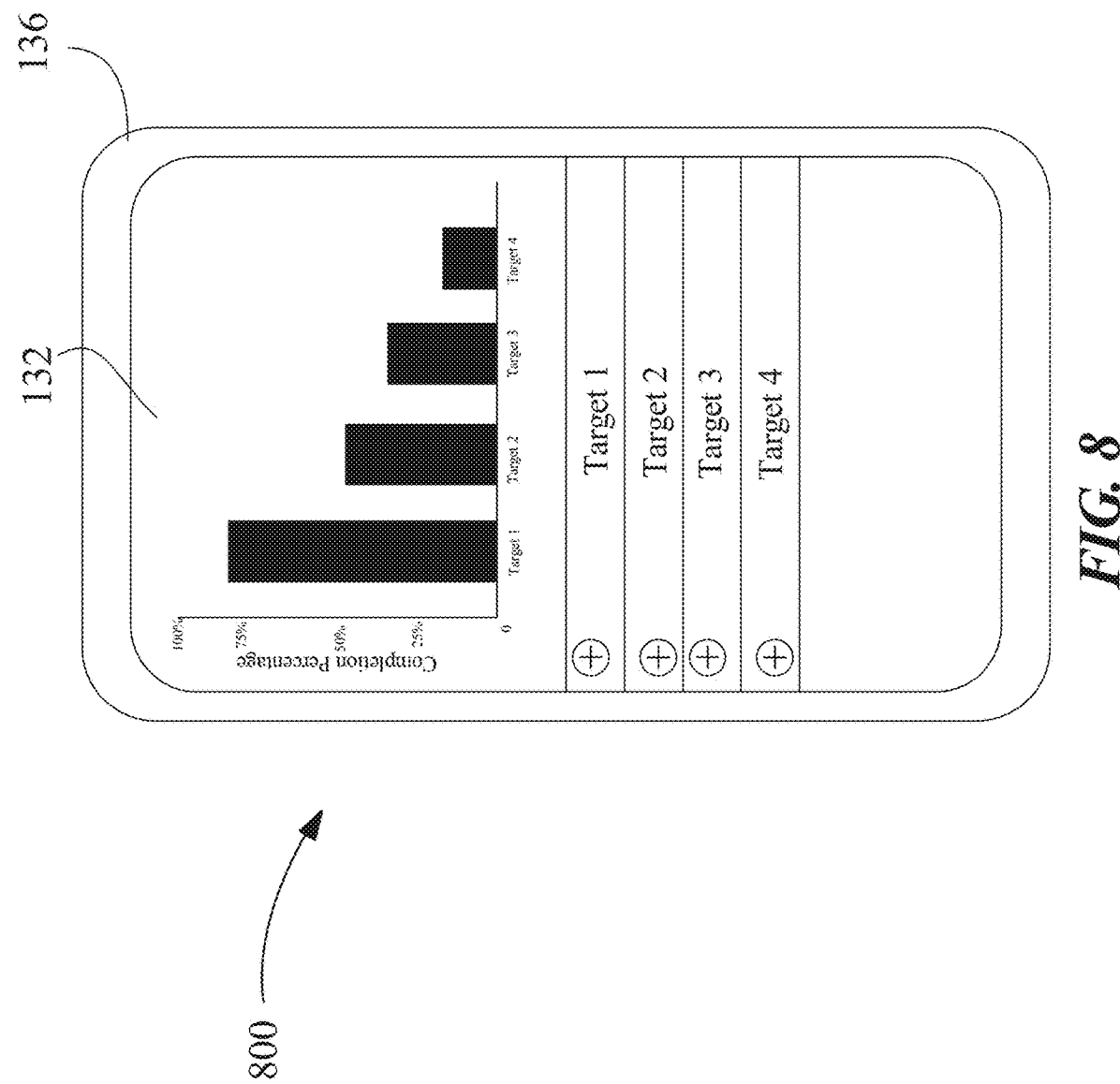
FIG. 8 is an exemplary embodiment of a user interface component.

Now referring to FIG. 8, an exemplary representation of a user interface component is presented. User interface 800 may include a display device such as display device 136. In an embodiment, user interface 800 may display a plurality of personal targets 132, which may be displayed in temporal order. A listing of personal targets 132 may additionally identify the percentage of completion of each personal target of the plurality of personal targets 132. In an embodiment, user interface 800 may display a detailed account of how the forecast data 120 is generated as a function of the tenured data 116. In an example, without limitations, user interface 800 may display a prediction of the lifespan of the user along with the user's health status and pecuniary status. In some embodiments, user interface 800 may display an a plurality of questions which require the user to enter information regarding the user profile 108 and user data 112. User interface 800 may present a user questions to determine the user target. In some embodiments, user interface 800 may be configured to display a plurality of personal targets 132 and their current completion percentage. As a user completes more personal targets 132 the display of user interface 800 may be updated.

Figure 9:
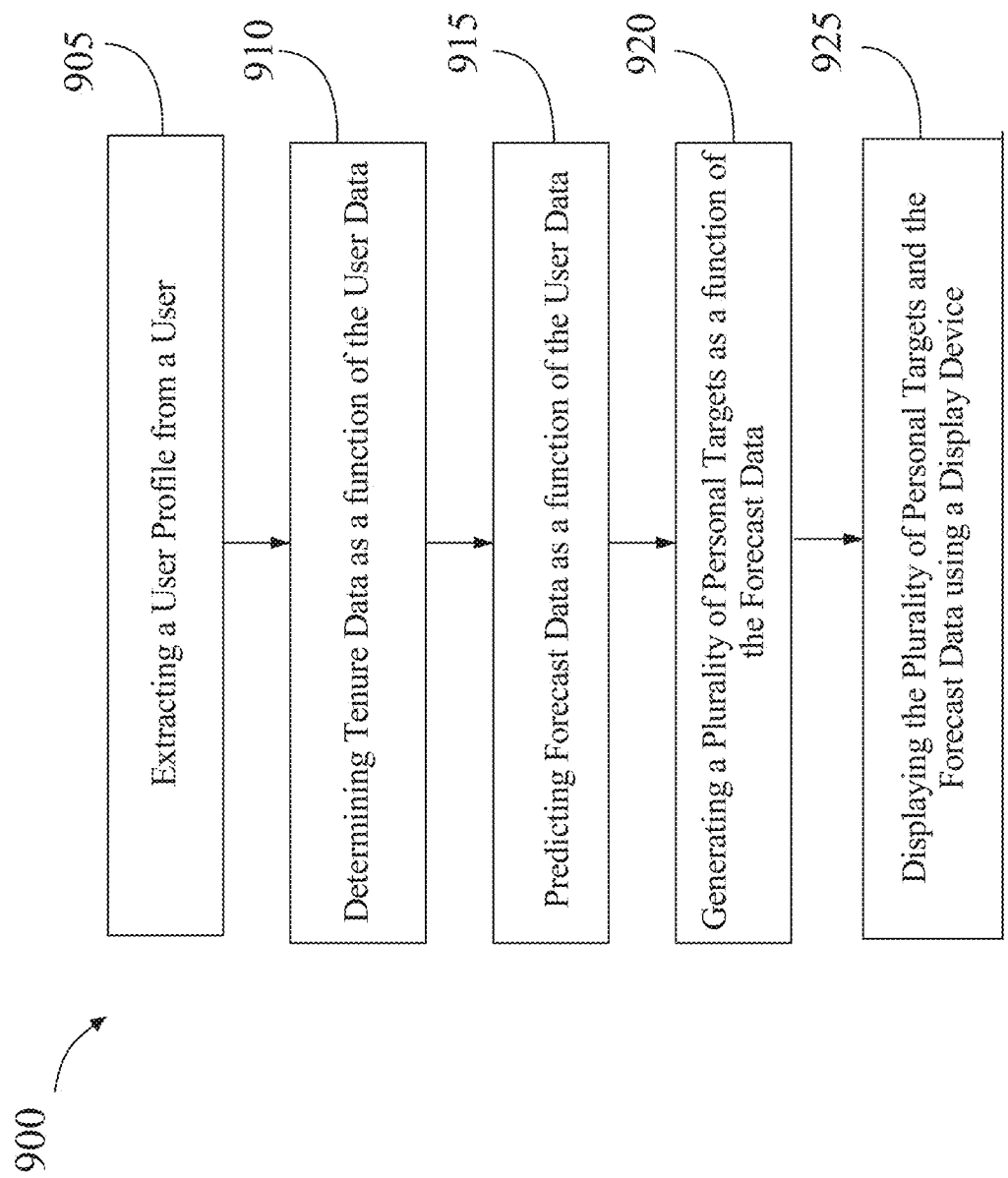
FIG. 9 is a flow diagram of an exemplary method for the generation of a plurality of personal targets.

Referring now to FIG. 9, a flow diagram of an exemplary method 900 for the generation of a plurality of personal targets is illustrated. At step 905, method 900 includes extracting, using at least a processor, a user profile from a user, wherein a user profile comprises a plurality of user data. This may be implemented as described and with reference to FIGS. 1-9. In some embodiments, extracting the user profile may comprise extracting the user profile using a Web crawler or a chatbot. In an embodiment, a plurality of user data may include biological data associated with the user. In another embodiment, extracting the user profile may comprise extracting the user profile using at least a sensor, wherein the at least a sensor comprises a wearable device Still referring to FIG. 9, At step 910, method 900 includes determining, using the at least a processor, tenure data as a function of the user data. This may be implemented as described and with reference to FIGS. 1-9.

Still referring to FIG. 9, At step 915, method 900 includes predicting, using the at least a processor, forecast data as a function of the tenure data. This may be implemented as described and with reference to FIGS. 1-9. In an embodiment, a forecast data may comprise a pecuniary status and/or a lifestyle status. In another embodiment, predicting the forecast data may comprise predicting the forecast data using a forecast machine-learning model. Predicting the forecast data using a forecast machine-learning model comprises training the forecast machine learning model using forecast training data, wherein the forecast training data contains a plurality of data entries containing the user data and the tenure data as inputs correlated to the forecast data as outputs and predicting forecast data as a function of the tenure data and the user data using the trained forecast machine learning model.

Still referring to FIG. 9, At step 920, method 900 includes generating, using the at least a processor, a plurality of personal targets as a function of the forecast data, wherein each personal target of the plurality of personal targets are associated with a timeline of the user. This may be implemented as described and with reference to FIGS. 1-9. In an embodiment, the plurality of personal targets may comprise at least a health target.

Still referring to FIG. 9, At step 925, method 900 includes displaying, using a display device, the plurality of personal targets and the forecast data. This may be implemented as described and with reference to FIGS. 1-8.

It is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 10:
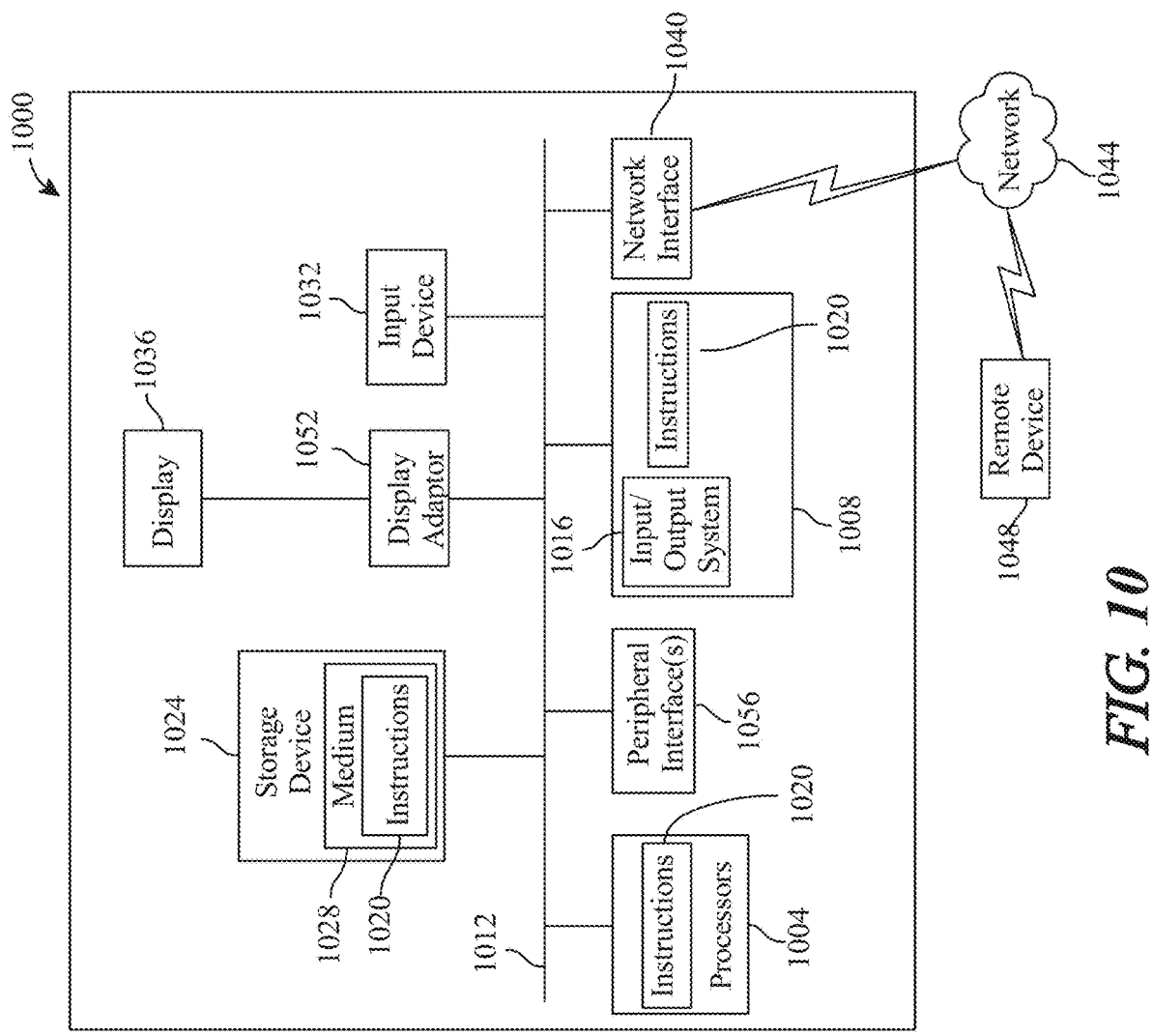
FIG. 10 is a block diagram of a computing system that can be used to implement any one or more of the methodologies disclosed herein and any one or more portions thereof.

FIG. 10 shows a diagrammatic representation of one embodiment of a computing device in the exemplary form of a computer system 1000 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 1000 includes a processor 1004 and a memory 1008 that communicate with each other, and with other components, via a bus 1012. Bus 1012 may include any of several types of bus structures including, but not limited to, a memory bus, a memory controller, a peripheral bus, a local bus, and any combinations thereof, using any of a variety of bus architectures.

Processor 1004 may include any suitable processor, such as without limitation a processor incorporating logical circuitry for performing arithmetic and logical operations, such as an arithmetic and logic unit (ALU), which may be regulated with a state machine and directed by operational inputs from memory and/or sensors; processor 1004 may be organized according to Von Neumann and/or Harvard architecture as a non-limiting example. Processor 1004 may include, incorporate, and/or be incorporated in, without limitation, a microcontroller, microprocessor, digital signal processor (DSP), Field Programmable Gate Array (FPGA), Complex Programmable Logic Device (CPLD), Graphical Processing Unit (GPU), general purpose GPU, Tensor Processing Unit (TPU), analog or mixed signal processor, Trusted Platform Module (TPM), a floating point unit (FPU), and/or system on a chip (SoC).

Memory 1008 may include various components (e.g., machine-readable media) including, but not limited to, a random-access memory component, a read only component, and any combinations thereof. In one example, a basic input/output system 1016 (BIOS), including basic routines that help to transfer information between elements within computer system 1000, such as during start-up, may be stored in memory 1008. Memory 1008 may also include (e.g., stored on one or more machine-readable media) instructions (e.g., software) 1020 embodying any one or more of the aspects and/or methodologies of the present disclosure. In another example, memory 1008 may further include any number of program modules including, but not limited to, an operating system, one or more application programs, other program modules, program data, and any combinations thereof.

Computer system 1000 may also include a storage device 1024. Examples of a storage device (e.g., storage device 1024) include, but are not limited to, a hard disk drive, a magnetic disk drive, an optical disc drive in combination with an optical medium, a solid-state memory device, and any combinations thereof. Storage device 1024 may be connected to bus 1012 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 1024 (or one or more components thereof) may be removably interfaced with computer system 1000 (e.g., via an external port connector (not shown)). Particularly, storage device 1024 and an associated machine-readable medium 1028 may provide nonvolatile and/or volatile storage of machine-readable instructions, data structures, program modules, and/or other data for computer system 1000. In one example, software 1020 may reside, completely or partially, within machine-readable medium 1028. In another example, software 1020 may reside, completely or partially, within processor 1004.

Computer system 1000 may also include an input device 1032. In one example, a user of computer system 1000 may enter commands and/or other information into computer system 1000 via input device 1032. Examples of an input device 1032 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 1032 may be interfaced to bus 1012 via any of a variety of interfaces (not shown) including, but not limited to, a serial interface, a parallel interface, a game port, a USB interface, a FIREWIRE interface, a direct interface to bus 1012, and any combinations thereof. Input device 1032 may include a touch screen interface that may be a part of or separate from display 1036, discussed further below. Input device 1032 may be utilized as a user selection device for selecting one or more graphical representations in a graphical interface as described above.

A user may also input commands and/or other information to computer system 1000 via storage device 1024 (e.g., a removable disk drive, a flash drive, etc.) and/or network interface device 1040. A network interface device, such as network interface device 1040, may be utilized for connecting computer system 1000 to one or more of a variety of networks, such as network 1044, and one or more remote devices 1048 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 1044, may employ a wired and/or a wireless mode of communication. In general, any network topology may be used. Information (e.g., data, software 1020, etc.) may be communicated to and/or from computer system 1000 via network interface device 1040.

Computer system 1000 may further include a video display adapter 1052 for communicating a displayable image to a display device, such as display device 1036. Examples of a display device include, but are not limited to, a liquid crystal display (LCD), a cathode ray tube (CRT), a plasma display, a light emitting diode (LED) display, and any combinations thereof. Display adapter 1052 and display device 1036 may be utilized in combination with processor 1004 to provide graphical representations of aspects of the present disclosure. In addition to a display device, computer system 1000 may include one or more other peripheral output devices including, but not limited to, an audio speaker, a printer, and any combinations thereof. Such peripheral output devices may be connected to bus 1012 via a peripheral interface 1056. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods, systems, and software according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. An apparatus for generation of a plurality of personal targets, wherein the apparatus comprises:
   at least a processor; and
   a memory communicatively connected to the at least a processor, wherein the memory contains instructions configuring the at least a processor to:
      receive a user profile from a user, wherein the user profile comprises a plurality of user data, wherein:
         receiving the user profile comprises extracting the user profile using at least a sensor;
         the at least a sensor comprises a wearable device; and
         the at least a sensor is configured to transform a property of an analyte in body liquid into a measurable signal that is proportional to a concentration of the analyte in the body liquid, wherein:
            transforming the property of the analyte in the body liquid into the measurable signal comprises detecting an analyte molecule in a selective way by transforming the detection into an analytical electrical signal; and
            the concentration of the analyte in the body liquid comprises a glucose concentration in the body liquid;
      determine tenure data as a function of the plurality of user data, wherein the plurality of user data comprises physiological data represented as a value on a numerical score range utilizing a tenure machine-learning model and further comprising:
         receiving tenure training data, wherein the tenure training data correlates the plurality of user data to a plurality of examples of physiological data;
         training the tenure machine-learning model using the tenure training data; and
         generating the tenure data using the tenure machine-learning model;
         adjusting the numerical score range using a linguistic value according to a severity of a condition;
      predict forecast data as a function of the tenure data and the plurality of user data utilizing a forecast machine-learning model which comprises:
         receiving forecast training data, wherein the forecast training data correlates the plurality of user data and tenure data to a plurality of forecast data;
         training the forecast machine-learning model using the forecast training data; and
         generating the forecast data as a function of the plurality of user data, tenure data and forecast data;
      generate a plurality of personal targets as a function of the forecast data, wherein each personal target of the plurality of personal targets is associated with a timeline of the user; and
      display the plurality of personal targets and the forecast data using a display device.

2. The apparatus of claim 1, wherein receiving the user profile comprises extracting the user profile using a web crawler.

3. The apparatus of claim 1, wherein receiving the user profile comprises extracting the user profile using a chatbot.

4. The apparatus of claim 1, wherein the plurality of user data comprises biological data associated with the user.

5. The apparatus of claim 1, wherein the plurality of personal targets comprises at least a health target.

6. The apparatus of claim 1, wherein the forecast data additionally comprises a pecuniary status.

7. The apparatus of claim 1, wherein the forecast data additionally comprises a lifestyle status.

8. A method for generation of a plurality of personal targets, wherein the method comprises:
   receiving, using at least a processor, a user profile from a user, wherein the user profile comprises a plurality of user data, wherein:
      receiving the user profile comprises extracting the user profile using at least a sensor;
      the at least a sensor comprises a wearable device; and
      the at least a sensor is configured to transform a property of an analyte in body liquid into a measurable signal that is proportional to a concentration of the analyte in the body liquid, wherein:
         transforming the property of the analyte in the body liquid into the measurable signal comprises detecting an analyte molecule in a selective way by transforming the detection into an analytical electrical signal; and
         the concentration of the analyte in the body liquid comprises a glucose concentration in the body liquid;
   determining, using the at least a processor, tenure data as a function of the plurality of user data, wherein the user data comprises physiological data represented as a value on a numerical score range utilizing a tenure machine-learning model and further comprising:
      receiving tenure training data, wherein the tenure training data correlates the plurality of user data to a plurality of examples of physiological data;
      training the tenure machine-learning model using the tenure training data; and
      generating the tenure data using the tenure machine-learning model;
      adjusting the numerical score range using a linguistic value according to a severity of a condition;
   predicting, using the at least a processor, forecast data as a function of the tenure data utilizing a forecast machine-learning model which comprises:
      receiving forecast training data, wherein the forecast training data correlates the plurality of user data and tenure data to a plurality of forecast data;
      training the forecast machine-learning model using the forecast training data; and
      generating the forecast data as a function of the plurality of user data, tenure data and forecast data;
   generating, using the at least a processor, a plurality of personal targets as a function of the forecast data, wherein each personal target of the plurality of personal targets is associated with a timeline of the user; and
   displaying, using a display device, the plurality of personal targets and the forecast data.

9. The method of claim 8, wherein receiving the user profile comprises extracting the user profile using a web crawler.

10. The method of claim 8, wherein receiving the user profile comprises extracting the user profile using a chatbot.

11. The method of claim 8, wherein the plurality of user data comprises biological data associated with the user.

12. The method of claim 8, wherein the plurality of personal targets comprises at least a health target.

13. The method of claim 8, wherein the forecast data additionally comprises a pecuniary status.

14. The method of claim 8, wherein the forecast data additionally comprises a lifestyle status.

\* \* \* \* \*